(12) United States Patent
Whited et al.

(10) Patent No.: US 9,089,980 B2
(45) Date of Patent: Jul. 28, 2015

(54) POWER OPERATED ROTARY KNIFE WITH DISPOSABLE BLADE SUPPORT ASSEMBLY

(71) Applicant: Bettcher Industries, Inc., Birmingham, OH (US)

(72) Inventors: Jeffrey Alan Whited, Amherst, OH (US); David Curtis Ross, Elyria, OH (US); Dennis R. Seguin, Jr., North Olmsted, OH (US); Geoffrey D. Rapp, Westlake, OH (US)

(73) Assignee: Bettcher Industries, Inc., Birmingham, OH (US)

( * ) Notice: Subject to any disclaimer, the term of this patent is extended or adjusted under 35 U.S.C. 154(b) by 0 days.

(21) Appl. No.: 14/308,876

(22) Filed: Jun. 19, 2014

(65) Prior Publication Data

US 2014/0298965 A1     Oct. 9, 2014

Related U.S. Application Data

(62) Division of application No. 13/073,207, filed on Mar. 28, 2011, now Pat. No. 8,756,819.

(60) Provisional application No. 61/323,346, filed on Apr. 12, 2010.

(51) Int. Cl.
    *B26B 27/00*      (2006.01)
    *B26B 25/00*      (2006.01)

(52) U.S. Cl.
     CPC .................... *B26B 25/002* (2013.01)

(58) Field of Classification Search
     USPC .............. 30/276, 347, 329, 337, 349; 83/665, 83/666, 676, 13; 452/135–137, 149
See application file for complete search history.

(56) References Cited

U.S. PATENT DOCUMENTS

| 1,220,345 A | 3/1917 | Koster |
|---|---|---|
| 1,374,988 A | 4/1921 | Cooper |

(Continued)

FOREIGN PATENT DOCUMENTS

| EP | 0190827 A2 | 8/1986 |
|---|---|---|
| FR | 1216947 | 4/1960 |

OTHER PUBLICATIONS

Oct. 3, 2011 Decision and Opinion of the United States Court of Appeals for the Federal Circuit (Appeal No. 2011-1038, -1046) regarding the case styled *Bettcher Industries, Inc. v. Bunzl USA, Inc. and Bunzl Processor Distribution, LLC*, Case No. 3:08 CV 2423, U.S. District and Opinion relates to U.S. Pat. No. 7,000,325, which issued from U.S. Appl. No. 10/909,168. (47 pages).

(Continued)

*Primary Examiner* — Phong Nguyen
(74) *Attorney, Agent, or Firm* — Tarolli, Sundheim, Covell & Tummino LLP

(57) ABSTRACT

A power operated rotary knife having a reusable handle assembly and disposable blade support assembly including a head portion and a blade support portion extending from the head portion, wherein upon completion of a tissue debriding operation on a donor, the used blade support assembly is removed from the handle assembly and disposed of, the handle assembly is autoclaved/sterilized and a new, sterilized blade support assembly is affixed to the handle assembly prior to a subsequent use. The knife includes an attachment assembly to releasably attach the disposable blade support assembly to the handle assembly and a retainer structure positioned in an annular groove formed in a bottom surface of the blade housing portion, the retainer structure bearing against an annular rotary knife blade and the blade housing portion to permanently retain an annular body section of the blade in the annular groove.

20 Claims, 23 Drawing Sheets

(56) References Cited

U.S. PATENT DOCUMENTS

| | | | |
|---|---|---|---|
| 1,476,345 A | 9/1922 | McGee | |
| 2,123,712 A | 7/1938 | Clark | |
| 2,266,888 A | 12/1941 | McCurdy et al. | |
| 2,827,657 A | 3/1958 | Bettcher | |
| RE25,947 E | 12/1965 | Bettcher | |
| 3,269,010 A | 8/1966 | Bettcher | |
| 4,082,232 A | 4/1978 | Brewer | |
| 4,170,063 A | 10/1979 | Bettcher | |
| 4,178,683 A | 12/1979 | Bettcher | |
| 4,198,750 A | 4/1980 | Bettcher | |
| 4,236,531 A | 12/1980 | McCullough | |
| 4,267,759 A | 5/1981 | Sullivan et al. | |
| 4,326,361 A | 4/1982 | McGill | |
| 4,363,170 A * | 12/1982 | McCullough | 30/276 |
| 4,439,924 A | 4/1984 | Bettcher | |
| 4,448,101 A | 5/1984 | Templeton | |
| 4,494,311 A | 1/1985 | McCullough | |
| 4,509,261 A | 4/1985 | Bettcher | |
| 4,516,323 A | 5/1985 | Bettcher et al. | |
| 4,575,938 A | 3/1986 | McCullough | |
| 4,609,227 A | 9/1986 | Wild et al. | |
| 4,637,140 A | 1/1987 | Bettcher | |
| 4,829,860 A | 5/1989 | VanderPol | |
| 4,854,046 A | 8/1989 | Decker et al. | |
| 4,909,640 A | 3/1990 | Nakanishi | |
| 5,099,721 A | 3/1992 | Decker et al. | |
| 5,230,154 A | 7/1993 | Decker et al. | |
| 5,331,877 A | 7/1994 | Ishii | |
| 5,419,619 A | 5/1995 | Lew | |
| 5,522,142 A | 6/1996 | Whited | |
| 5,529,532 A | 6/1996 | Desrosiers | |
| 5,664,332 A | 9/1997 | Whited et al. | |
| 5,692,307 A | 12/1997 | Whited et al. | |
| 5,761,817 A | 6/1998 | Whited et al. | |
| 5,971,413 A | 10/1999 | El-Kassouf | |
| 6,070,945 A | 6/2000 | Ritchey et al. | |
| 6,354,949 B1 | 3/2002 | Baris et al. | |
| 6,751,872 B1 | 6/2004 | Whited et al. | |
| 6,769,184 B1 | 8/2004 | Whited | |
| 6,978,548 B2 | 12/2005 | Whited et al. | |
| 7,000,325 B2 | 2/2006 | Whited | |
| 8,756,819 B2 | 6/2014 | Whited et al. | |
| 2002/0096027 A1 | 7/2002 | Whited et al. | |
| 2003/0131482 A1 | 7/2003 | Long et al. | |
| 2007/0283573 A1 | 12/2007 | Levsen | |
| 2008/0098605 A1 * | 5/2008 | Whited et al. | 30/276 |
| 2008/0183109 A1 | 7/2008 | Babaev | |
| 2009/0227192 A1 | 9/2009 | Luthi et al. | |

OTHER PUBLICATIONS

European Search Report dated Aug. 26, 2013 for European patent application No. 11769309.3, filed Nov. 12, 2012, European patent application No. 11769309.3 is a national phase application of PCT International Patent Application No. PCT/US2011/031196, filed Apr. 5, 2011, PCT International Application No. PCT/US2011/031196 claims priority from U.S. Appl. No. 13/073,207 is the parent of the present divisional application and issued as U.S. Pat. No. 8,756,819 on Jun. 24, 2014. (9 pages).

European Search Report dated Aug. 26, 2013 for European patent application No. 11769309.3, filed Nov. 12, 2012, European patent application No. 11769309.3 is a national phase application of PCT International Patent Application No. PCT/US2011/031196, filed Apr. 5, 2011, PCT International Application No. PCT/US2011/031196 corresponds to and claims priority from U.S. Appl. No. 13/073,207, filed Mar. 28, 2011. U.S. Appl. No. 13/073,207 is the parent of the present divisional application and issued as U.S. Pat. No. 8,756,819 on Jun. 24, 2014. (12 pages).

* cited by examiner

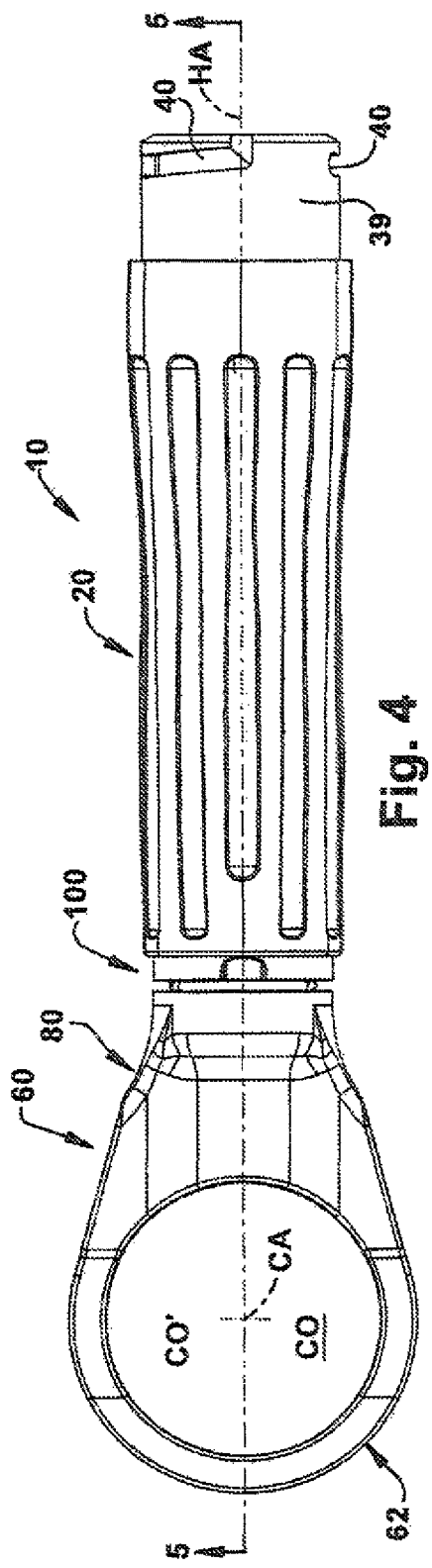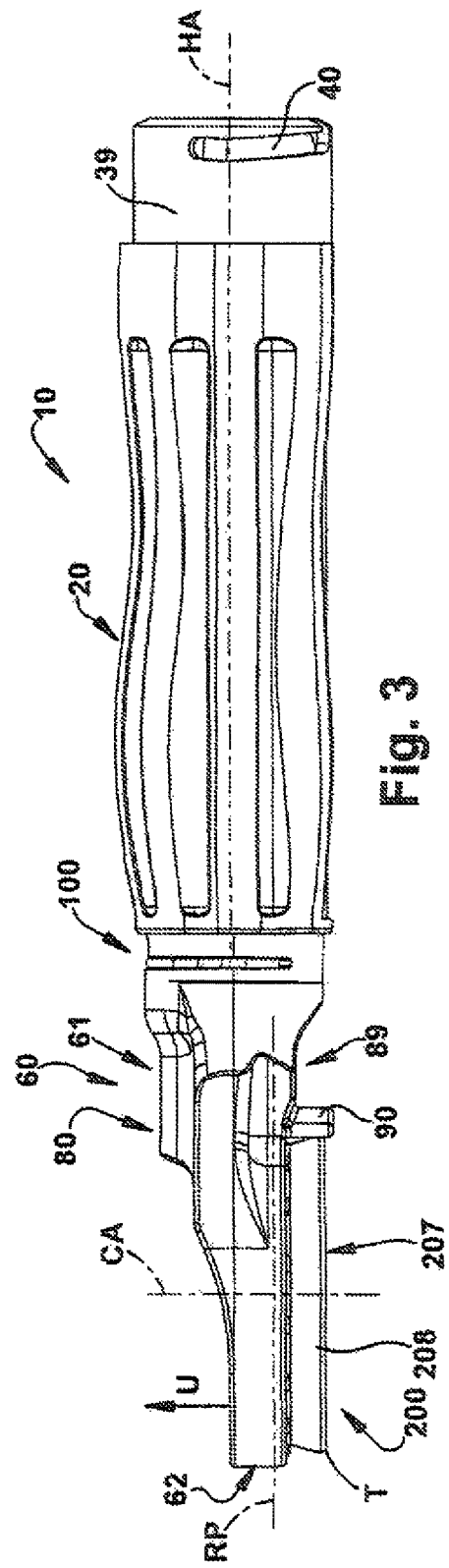

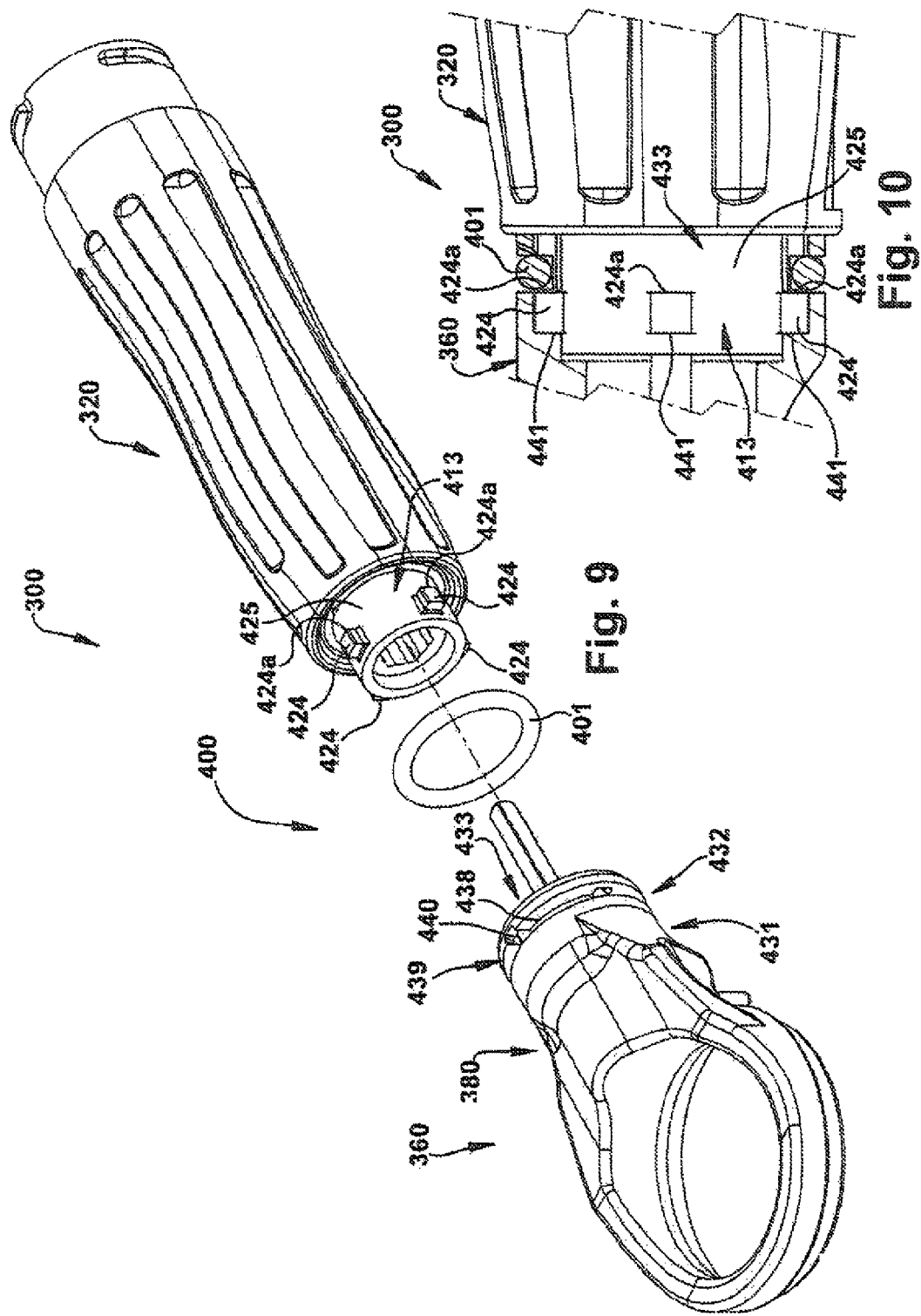

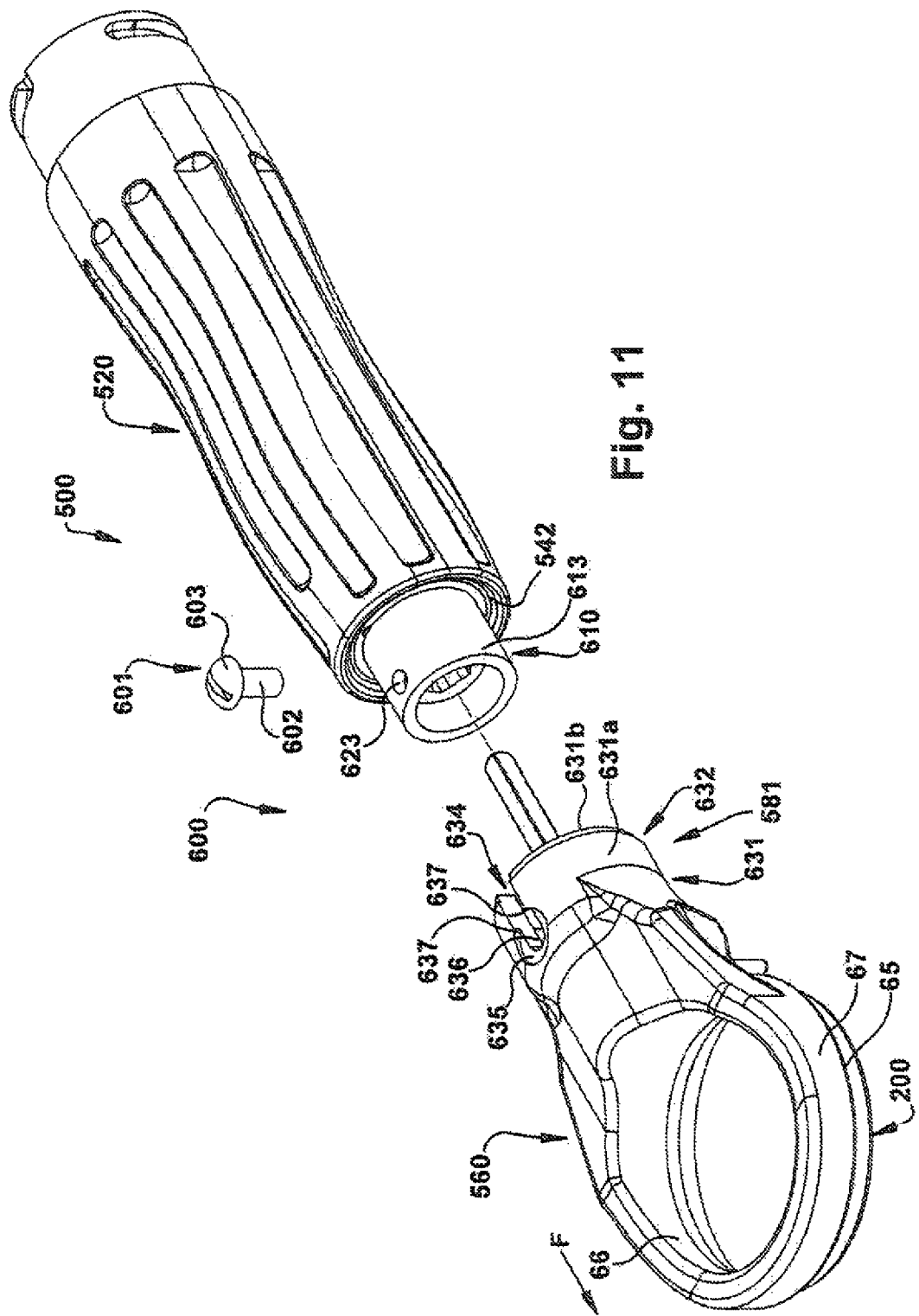

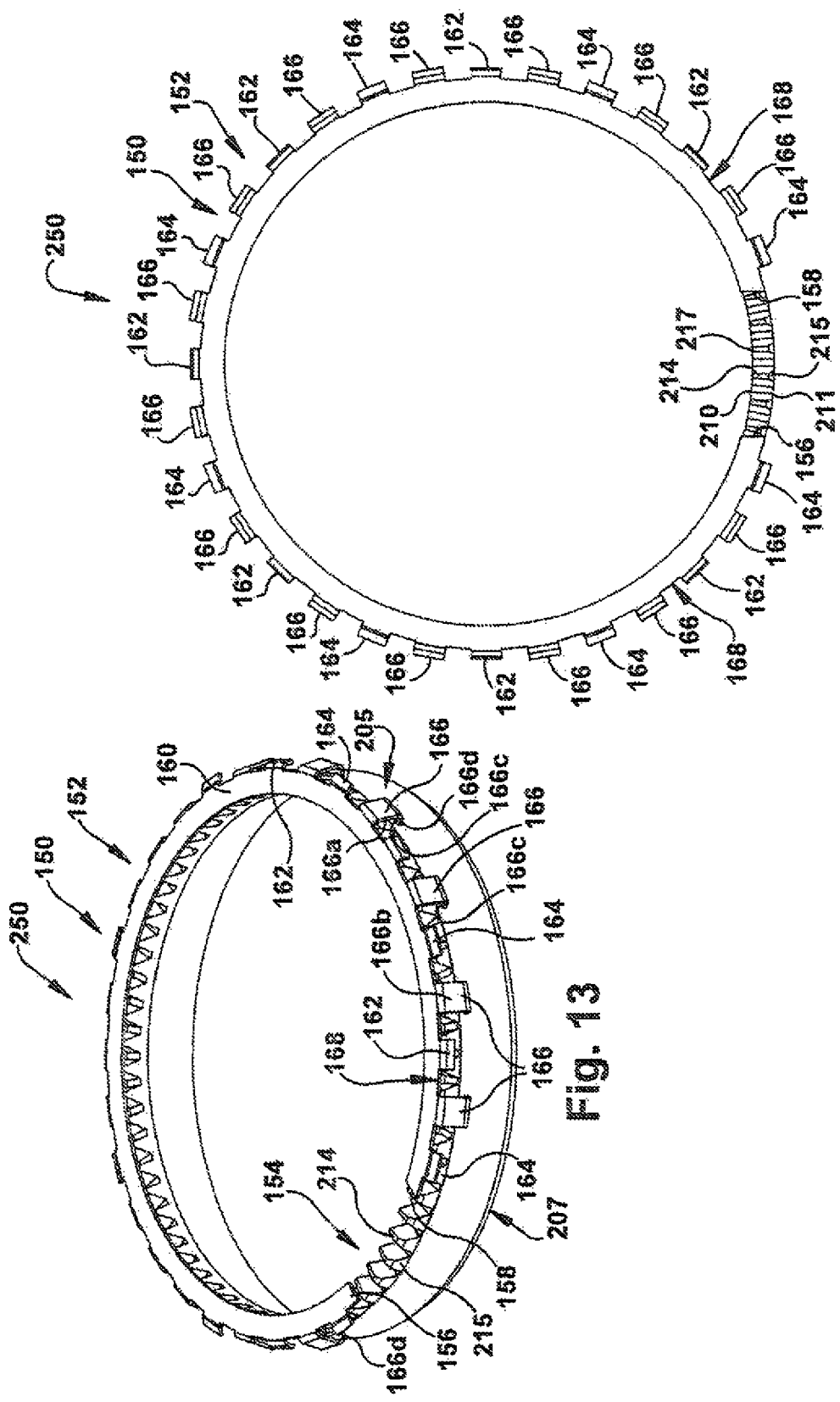

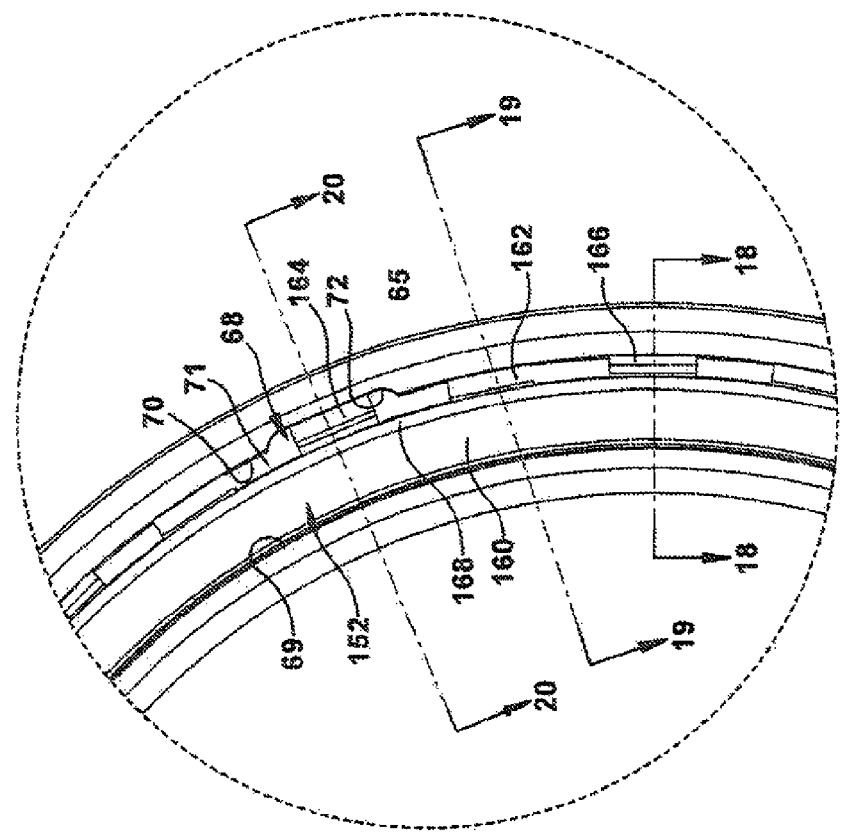
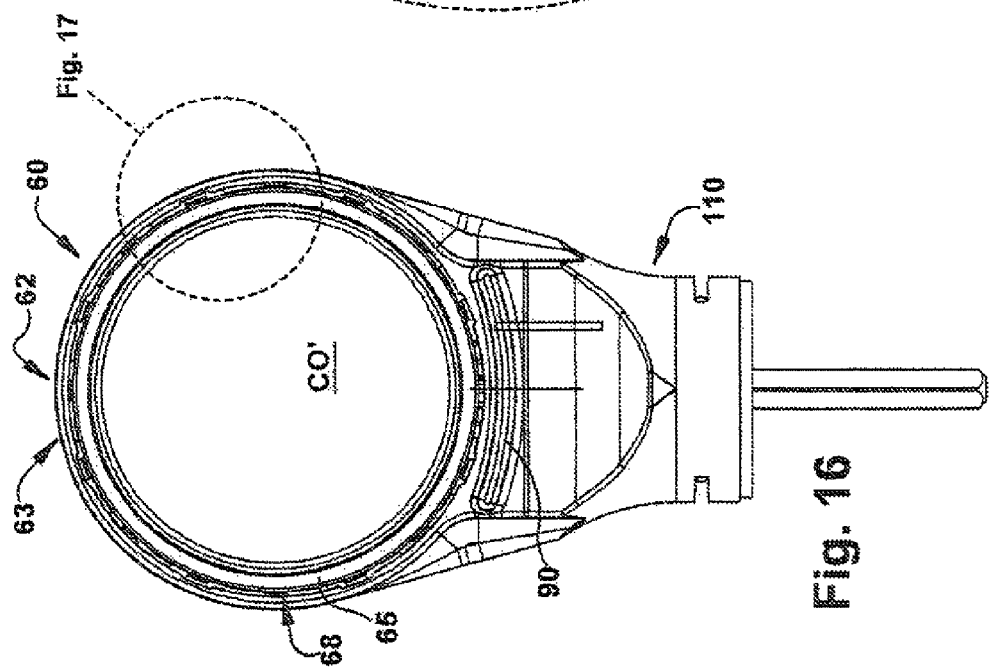

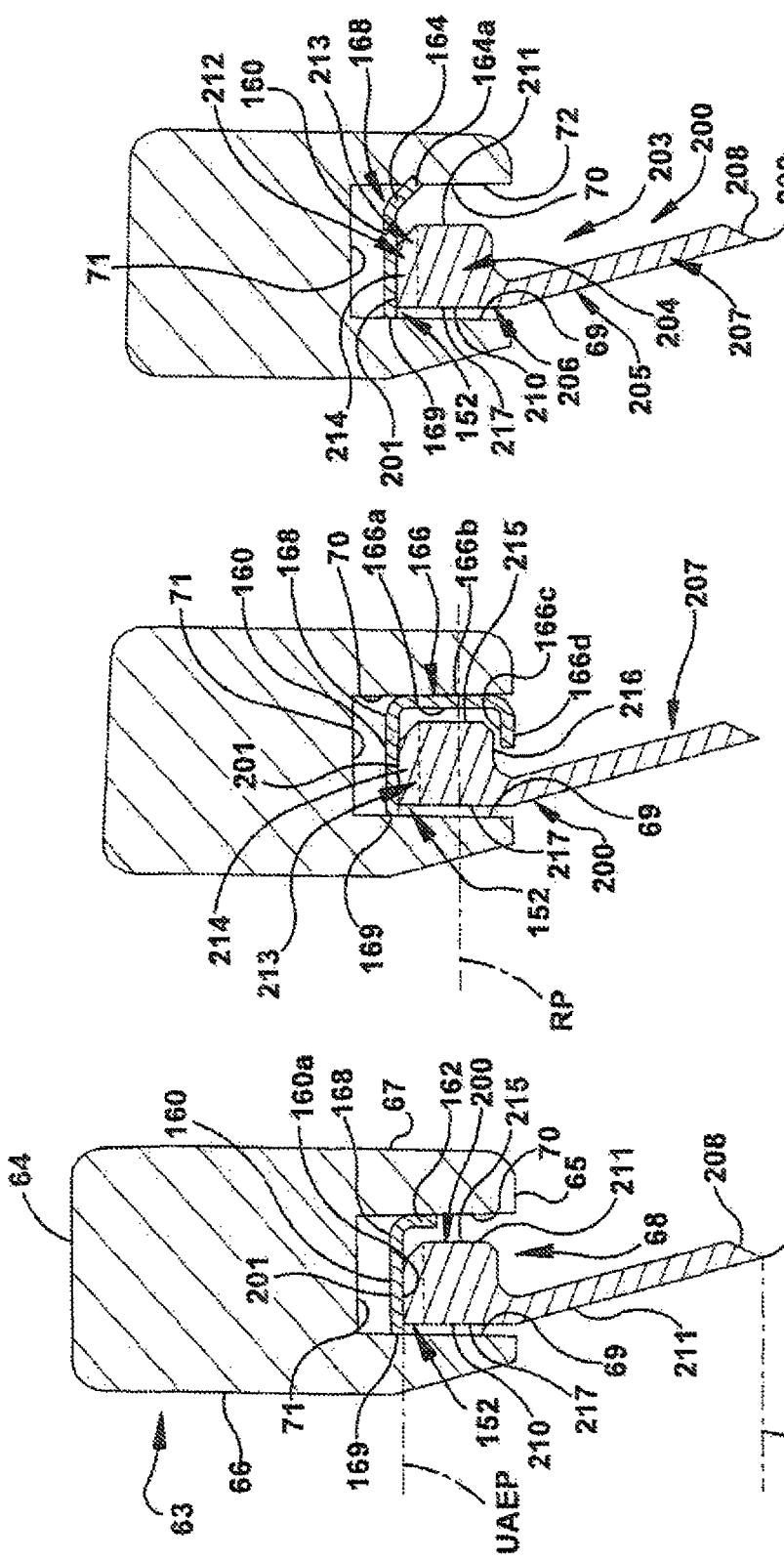

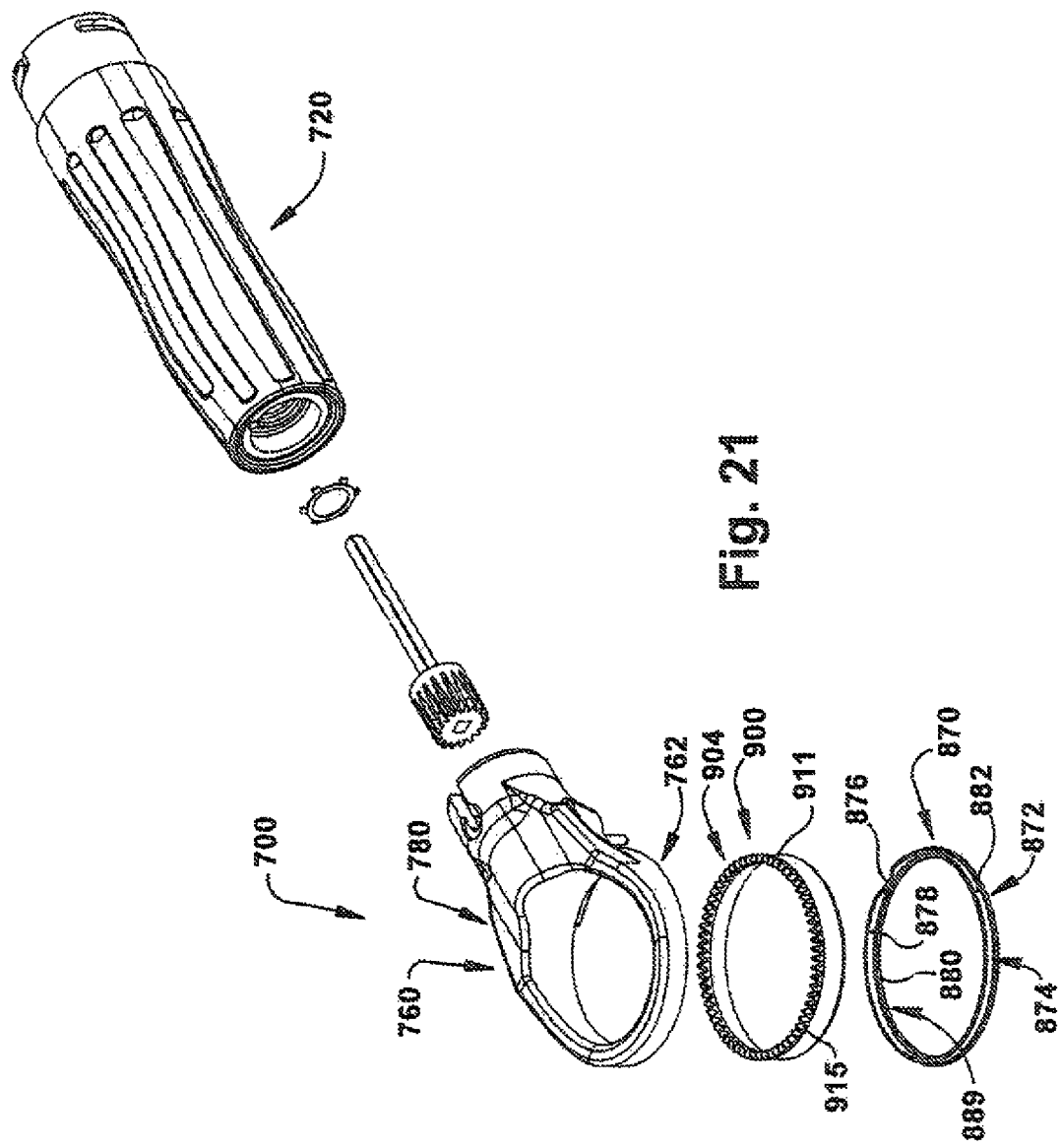

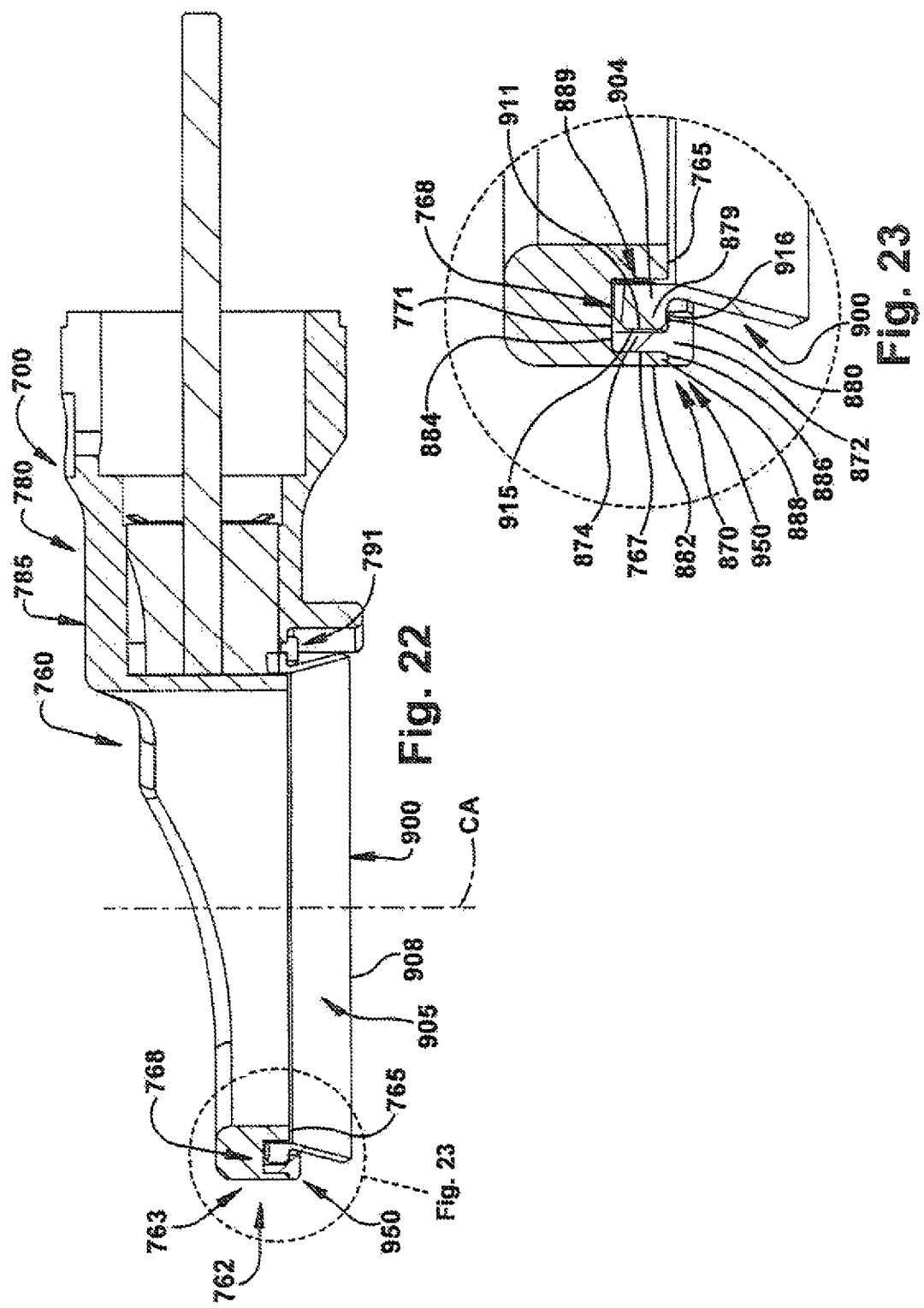

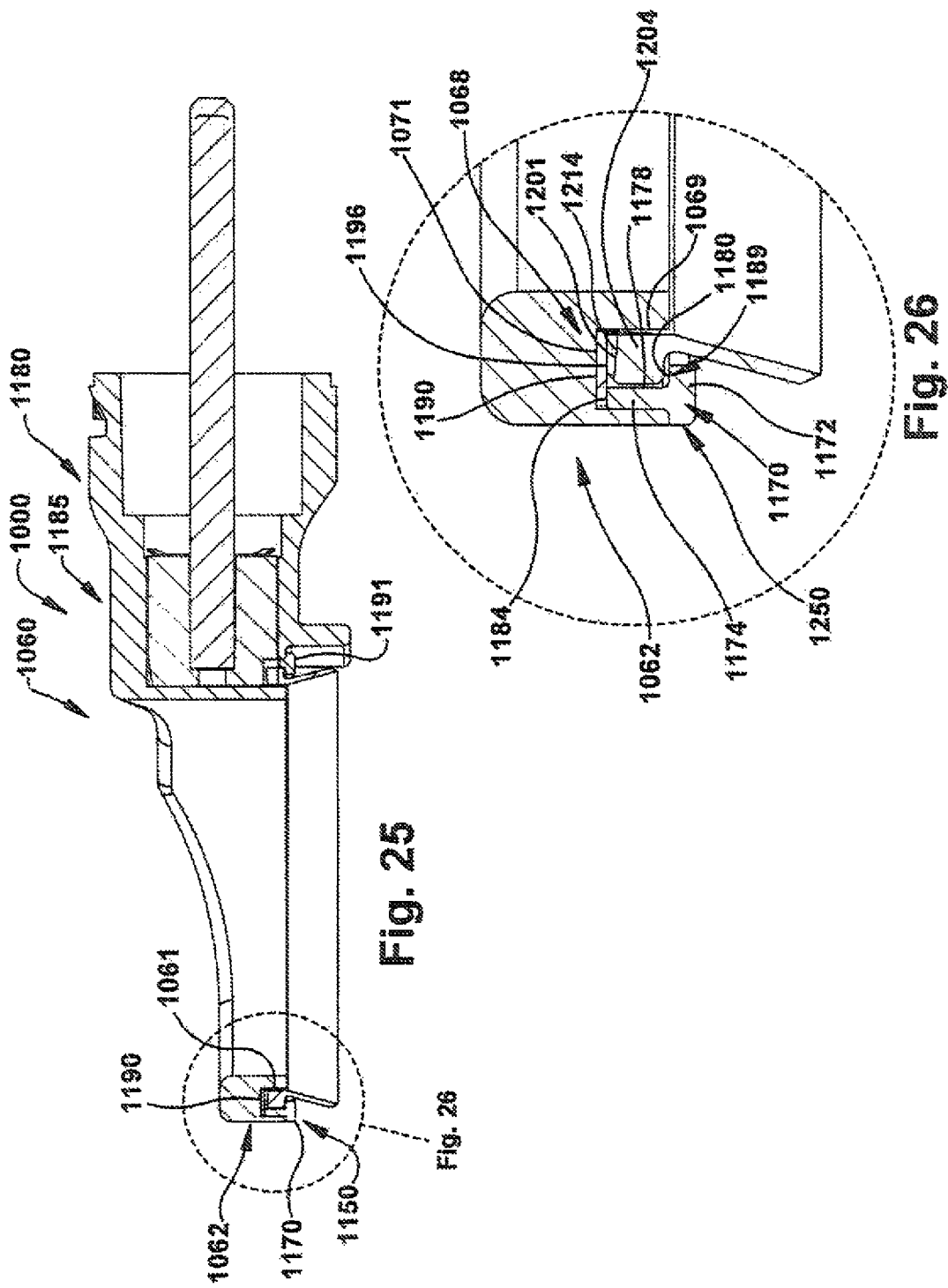

POWER OPERATED ROTARY KNIFE WITH DISPOSABLE BLADE SUPPORT ASSEMBLY

CROSS-REFERENCE TO RELATED APPLICATION

This application claims priority to and is a division of currently pending U.S. Non-Provisional application Ser. No. 13/073,207, filed on Mar. 28, 2011, published as U.S. Publication No. US-2011-0247220-A1 on Oct. 13, 2011, issuing as U.S. Pat. No. 8,756,819 on Jun. 24, 2014, which claims priority from U.S. Provisional Application Ser. No. 61/323,346, filed on Apr. 12, 2010. U.S. application Ser. No. 13/073,207 and U.S. Publication No. US-2011-0247220-A1 and U.S. Application Ser. No. 61/323,346 are incorporated herein in their respective entireties by reference for any and all purposes.

TECHNICAL FIELD

The present disclosure relates to a method and apparatus for using a power operated rotary knife to debride tissue from recovered bones of a human donor and, more specifically, to a power operated rotary knife having a reusable handle assembly and disposable blade support assembly, wherein upon completion of a debriding tissue operation on the recovered bones of a donor, the used blade support assembly is removed from the handle assembly and disposed of, the handle assembly is autoclaved/sterilized and a new, sterilized blade support assembly is affixed to the handle assembly prior to a subsequent use.

BACKGROUND

Power operated rotary knives are widely used in meat processing facilities for meat cutting and trimming operations. Such power operated rotary knives typically include a handle assembly including a head member extending from the handle assembly, an annular blade housing coupled to the head member via a clamp assembly, and an annular rotary blade supported for rotation by the blade housing. The annular rotary blade of a conventional power operated rotary is rotated by a drive mechanism including a flexible drive shaft which extends through an opening in the handle assembly and engages a pinion gear supported in a distal portion of the handle assembly head member. The flexible drive shaft includes a stationary outer sheath and a rotatable interior drive shaft which is driven by a pneumatic or electric motor. Gear teeth of the pinion gear engage mating gear teeth formed on an upper surface of the annular rotary blade. Upon rotation of the pinion gear by the flexible drive shaft, the annular rotary blade rotates within the blade housing at a high RPM, on the order of 1,500-2,000 RPMs. Conventional power operated rotary knives are disclosed in U.S. Pat. No. 6,354,949 to Baris et al., U.S. Pat. No. 6,751,872 to Whited et al., U.S. Pat. No. 6,769,184 to Whited, and U.S. Pat. No. 6,978,548 to Whited et al., all of which are assigned to the assignee of the present invention and all of which are incorporated herein in their respective entireties by reference.

Due to advances in biomedical technology, tissue engineering and the ability to safely sterilize musculoskeletal tissue, there is an increasing demand for more donated human tissue. Musculoskeletal, cardio-vascular, eye and skin/dermis are tissues commonly recovered for transplantation. Tissue processing agencies typically receive the tissue after legal consent is obtained under the Uniform Anatomical Gift Act (UAGA) and adopted state revisions from Food and Drug Administration (FDA) and the American Association of Tissue Banks (AATB) approved procurement agencies. After a comprehensive screening process, the tissue may be used for transplantation purposes, medical research and/or medical education. Long bone of the human body, e.g., femurs are especially valuable due to their thicker cortical walls and therefore the ability to be manufactured into weight bearing spinal constructs. In some instances, bone marrow may also be extracted in order to create stem cell infused bone products which promote incorporation and healing. In many instances, soft tissues of the lower extremities may also be recovered for transplantation purposes such as the gracilis, semitendinosus, achilles and knee tendons. Requirements for successfully recovering human donor bones are stringent, both in terms of the very limited time period after death in which bones can be successfully recovered after death of the donor (typically, within 24 hours after death) and in terms of conditions of sterility required during the bone harvesting process. The sterility required for harvesting of human donor body parts is akin to the sterility required during human surgery.

Under the AATB guidelines, human bone must be recovered within 24 hours of the documented time of death if the body is refrigerated and within 15 hours of the documented time of death if the body is not refrigerated. Under established rules, if a death occurs in a hospital, the decedent must be referred for evaluation of organ/tissue donation to the hospital's designated Organ Procurement Organization (OPO). The OPO may have their own tissue recovery team or may elect to refer to a contracted tissue and eye recovery agency for medical suitability evaluation. If the donor is medically cleared for donation, tissue is recovered by trained technicians in a clean environment utilizing sterile disposable drapes and instrumentation. The tissue is generally recovered in "zone" or, at the location of the donor, cultured and individually placed in disposable sterile bags and stored on wet ice in validated shipping containers prior to shipment to a tissue processor.

Once the shipping container is received at a musculoskeletal tissue processing facility, the tissue is monitored for temperature and inventoried. Typically, the tissue is cultured, re-bagged and stored in freezers until serological, microbiological and fungal test results are completed. Additionally, a full medical record review, to include the donor's medical/social history and post-mortem exam, if applicable, are reviewed by a medical doctor before the tissue is released for processing. Upon release, the tissue is thawed and moved to technicians who engage in debriding the bone. Debriding is the process that involves removing tissue such as muscle, ligaments, tendons, adipose and other tissue from the recovered bone. After debriding the bones, the recovered, debrided bones are placed in a container having a low temperature interior region to preserve the recovered bones placed in the container. Generally, no gross debridement with power tools is performed by recovery teams in the field. Processors prefer leg en-bloc recovery to prevent recovery team technicians from damaging tendons and meniscus. Gross debridement is performed by a separated technical team in a controlled environment at the musculoskeletal tissue processing facility, e.g., AlloSource, Regeneration Technologies, Inc. or Musculoskeletal Transplant Foundation.

With regard to recovery of full thickness skin or dermis, the removal of the upper dermal layer and fat is required prior to processing. This is also referred to as debriding tissue. Such an upper layer of skin tissue from the donor's abdomen and buttocks areas may be used as, for example, a cover or dressing for severely burned areas of a burn patient.

Typical instruments used for removing or debriding tissue from recovered bones include scalpels, stainless steel medical chisels, and power operated tools having disposable, stainless steel brushes wherein the brush bristles scour away tissue from the surface of the recovered bones. Additionally, a liquid may be applied to a recovered bone to soften attached tissue prior to debriding. Unfortunately, use of all of scalpels, chisels and power operated brushes is slow, time consuming and tedious. The tissue debriding process may include multiple steps: first larger pieces of tissue adhering to a recovered bone may be removed with a chisel; remaining smaller pieces of tissue may be cut away with a scalpel; finally, remaining tissue may be scoured away with a power operated brush.

Further, since insuring sterility in the recovery process and avoiding the possibility cross contamination between donors is of paramount importance, the instruments used for tissue debriding must be sterilized prior to use and either: 1) disposable upon completion of the harvesting process for a given donor; or 2) capable of being autoclaved, that is, sterilized after use.

Utilizing power operated rotary knives would appear to have potential for use in various tissue removal and/or tissue recovery operations including, for example, debriding bones, debriding full thickness skin, recovery of tendons and ligaments, among others. However, the sterility requirements of the human donor recovery process raise issues and create problems that have effectively precluded the use of conventional power operated rotary knives in human donor recovery. The number of individual components of a conventional power operated rotary knife is large and the assembly/disassembly process is time-consuming. Thus, the time and cost to disassemble and sterilize all of the components of a conventional power operated rotary knife and then reassemble the knife under sterile conditions prior to use on a new donor would be problematic. Additionally, disposability of, for example, the annular rotary blade is not feasible economically, that is, the annular rotary blade of a conventional power operated rotary knife is simply too expensive to be discarded after use of the blade for a relatively short time on a single donor. When used in meat processing facilities, a typical annular rotary blade is resharpened numerous times and, when properly maintained, may be used for an extended period of time in the range of 50-100 hours or more, prior to being discarded.

What is needed is a power operated rotary knife that may be effectively used for tissue removal or tissue debriding in the recovery of human donor body parts, including, but not limited to bone debriding, full thickness skin debriding, and/or tendon/ligament recovery operations/processes. What is also needed is a power operated rotary knife that is cost effective for use in recovery of human donor body parts, including, but not limited to, tissue removal or debriding such as bone debriding, full thickness skin debriding, tendon/ligament harvesting operations/processes. What is also needed is a power operated rotary knife that would provide a reduced number of components, ease of sterilization of reusable components, and/or disposable components/assemblies. What is also needed is a power operated rotary knife that is easy to assembly and dissemble for sterilization purposes and/or replacement of disposable components/assemblies.

It should also be recognized, of course, that the foregoing is equally applicable to non-human donors. For example, certain animals, such as pigs, have body parts that may be useful to human patients and are, therefore, recovered for medical purposes. Thus, to the extent that tissue recovery operations such as debriding of bones, debriding of skin, tendon/ligament harvesting operations/processes are carried out on non-human donors, the method and apparatus of the present disclosure is equally applicable to and is intended to cover such non-human donors and associated recovery/harvesting operations/processes.

SUMMARY

The present disclosure relates to a method and apparatus for using a power operated rotary knife for tissue removal or debriding tissue in connection with tissue recovery operations such as, but not limited to, the debriding of bones, full thickness skin debriding, tendon/ligament recovery operations/processes from the body of a donor and, more specifically, to a power operated rotary knife having a reusable handle assembly and disposable blade support assembly, wherein upon completion of a tissue removal or debriding operation, the used blade support assembly is removed from the handle assembly and disposed of, the handle assembly is autoclaved/sterilized and a new, sterilized blade support assembly is affixed to the handle assembly prior to a subsequent use of the power operated rotary knife on a subsequent donor.

An exemplary embodiment of the present disclosure includes a disposable blade support assembly for a power operated rotary knife including a handle assembly including an elongated handle defining a longitudinal throughbore and an interface element at a distal end of the handle assembly along a longitudinal axis of the handle assembly. The disposable blade support assembly features: a head portion; a blade housing portion extending from a distal end of the head portion, the blade housing portion including an annular ring and defining an annular groove in a bottom surface of the annular ring; an annular rotary knife blade permanently supported for rotation within the annular groove of the blade housing portion, the blade having first and second axially spaced apart ends and an annular body extending therebetween, the annular body including an annular body support section adjacent the first end, the annular body support section defining a plurality of gear teeth at the first end, the annular body further including an annular blade section adjacent the second end, the annular blade section defining a cutting edge at the second edge; a drive gear mechanism rotatably supported within the head portion and including a plurality of gear teeth that mesh with the plurality of gear teeth of the annular body support section to rotate the blade; and a retainer structure including a retainer securing and rotatably supporting the annular body support section of the knife blade within the annular groove, the retainer permanently affixed within the annular groove. In one exemplary embodiment, the disposable blade support assembly includes an interface structure disposed at a proximal end of the blade support assembly, the interface structure engaging the interface element of the handle assembly to releasably attach the blade support assembly to the handle assembly.

Another exemplary embodiment of the present disclosure includes a power operated rotary knife featuring: a handle assembly including an elongated handle defining a longitudinal throughbore; a disposable blade support assembly including a head portion, a blade housing portion extending from the head portion, and an annular rotary knife blade permanently supported for rotation within the blade housing portion, the blade having first and second axially spaced apart ends and an annular body extending therebetween, the annular body including an annular body support section adjacent the first end, the annular body support section defining a plurality of gear teeth at the first end, the annular body further including an annular blade section adjacent the second end, the annular blade section defining a cutting edge at the second edge, the blade support assembly further including a drive gear mechanism rotatably supported within the head portion and including a plurality of gear teeth that mesh with the plurality of gear teeth of the annular body support section to rotate the blade; and an attachment assembly for releasably attaching the blade support assembly to the handle assembly, the attachment assembly including: an interface element at a distal end of the handle assembly along a longitudinal axis of the handle assembly; an interface structure disposed at a proximal end of the blade support assembly, and a retainer to releasably attach the blade support assembly to the handle assembly by coupling the interface element and the interface structure.

Another exemplary embodiment of the present disclosure includes an attachment assembly for releasably attaching a blade support assembly to a handle assembly of a power operated rotary knife. The attachment assembly features: an interface element disposed at a distal end of the handle assembly along a longitudinal axis of the handle assembly; an interface structure disposed at a proximal end of the blade support assembly, the socket defining an opening receiving the handle assembly interface projection when the blade support assembly is attached to the handle assembly, one of the interface element and the interface structure comprising an interface projection and the other of the interface element and the interface structure comprising a socket; and a retainer to releasably attach the blade support assembly to the handle assembly, one of the socket and the interface projection including a retainer receiver receiving a retainer and the other of the socket and the interface projection including a retainer bearing surface to bear against the retainer to prevent detachment of the blade support assembly and the handle assembly.

Another exemplary embodiment of the present disclosure includes a retainer structure for permanently retaining and supporting an annular rotary knife blade of a power operated rotary knife with an annular groove formed in a bottom surface of a blade housing portion of a blade support assembly of a power operated rotary knife, the retainer structure featuring a retainer permanently affixed within the annular groove, the retainer including: an upper wall; a first plurality of tabs; and a second plurality of tabs; wherein the first plurality of tabs extend radially outwardly and downwardly from the upper wall and are sized to have an interference fit with a radially outer wall of the annular groove to permanently affix the retainer within the annular groove; and further wherein the second plurality of tabs extend radially outwardly and downwardly from the upper wall, the second plurality of tabs each having first and second portions forming a generally L-shaped radially inwardly facing bearing race to rotatably support an annular body support section of the blade.

Another exemplary embodiment of the present disclosure includes a power operated rotary knife featuring: a handle assembly including an elongated handle defining a longitudinal throughbore; a disposable blade support assembly including a head portion and a blade housing portion extending from the head portion, the blade housing portion including an annular groove in a bottom surface of the blade housing portion, the annular groove is generally rectangular in cross section and is defined by an top wall and first and second opposing side walls, the first side wall being radially outwardly of the second side wall; an annular rotary knife blade permanently supported for rotation within the blade housing portion, the blade having a body section and an annular blade section extending angularly axially downwardly from a bottom surface of the body section, an upper surface of the body section defining a plurality of gear teeth; a drive gear mecha-nism supported within the head section and including a plurality of gear teeth that mesh with the plurality of gear teeth of the second end of the blade to rotate the blade; an attachment assembly to releasably attach the disposable blade support assembly to the handle assembly; and a retainer structure permanently affixed within the annular groove and providing at least two bearing surfaces to rotatably support the blade body section within the annular groove.

In one exemplary aspect, the present disclosure includes a method of debriding tissue utilizing a power operated rotary knife, the steps of the method featuring: a) providing a power operated rotary knife including: a handle assembly including an elongated handle defining a longitudinal throughbore, a disposable blade support assembly including a blade housing portion, a head portion, an annular rotary knife blade permanently supported for rotation within the blade housing portion, the blade having first and second ends spaced axially apart, the first end including an annular blade section and the second end defining a plurality of gear teeth, and a drive gear mechanism rotatably supported within the head portion and including a plurality of gear teeth that mesh with the plurality of gear teeth of the second end of the blade to rotate the blade, and an attachment assembly to releasably attach the blade support assembly to the handle assembly; b) using the power operated rotary knife to trim a layer of tissue; and c) removing the trimmed layer of tissue.

BRIEF DESCRIPTION OF THE DRAWINGS

The foregoing and other features and advantages of the present disclosure will become apparent to one skilled in the art to which the present disclosure relates upon consideration of the following description of the invention with reference to the accompanying drawings, wherein like reference numerals, unless otherwise described refer to like parts throughout the drawings and in which:

FIG. 3 is a schematic side elevation view of the power operated rotary knife of FIG. 1;

FIG. 4 is a schematic top plan view of the power operated rotary knife of FIG. 1;

FIG. 8 is a schematic side elevation view of the power operated rotary knife of FIG. 1 with the reusable handle assembly detached from the disposable blade support assembly to show the first handle attachment structure embodiment;

FIG. 9 is a schematic perspective view of another exemplary embodiment of a power operated rotary knife of the present disclosure including a second handle attachment structure exemplary embodiment for releasably coupling a disposable blade support assembly to a reusable handle assembly handle assembly;

FIG. 10 is a schematic longitudinal view, partly in section and partly in side elevation, of a portion of the power operated rotary knife of FIG. 9 showing the second handle attachment structure embodiment;

FIG. 11 is a schematic perspective view of another exemplary embodiment of a power operated rotary knife of the present disclosure including a third handle attachment structure exemplary embodiment for releasably coupling a disposable blade support assembly to a reusable handle assembly handle assembly;

FIG. 13 is a schematic perspective view of the annular rotary knife blade and the tabbed blade retainer structure of FIG. 12;

FIG. 14 is a schematic top plan view of the annular rotary knife blade and the tabbed blade retainer structure of FIG. 12;

FIG. 16 is a schematic bottom plan view of the disposable blade support assembly of FIG. 12 with the annular rotary knife blade and tabbed blade retainer structure supported within the blade support assembly;

FIG. 17 is a schematic, enlarged bottom plan view of a portion of the blade support assembly, the annular rotary knife blade, and the tabbed blade retainer structure of FIG. 16;

FIG. 18 is a schematic axial sectional view of the annular rotary knife blade, the tabbed blade retainer structure and the disposable blade support assembly, as seen from a plane indicated by the line 18-18 in FIG. 17;

FIG. 19 is a schematic axial sectional view of the annular rotary knife blade, the tabbed blade retainer structure and the disposable blade support assembly, as seen from a plane indicated by the line 19-19 in FIG. 17;

FIG. 20 is a schematic axial sectional view of the annular rotary knife blade, the tabbed blade retainer structure and the disposable blade support assembly, as seen from a plane indicated by the line 20-20 in FIG. 17;

FIG. 21 is a schematic perspective view of a portion of the power operated rotary knife of FIG. 1 showing a disposable blade support assembly and a second blade retainer structure exemplary embodiment to retain an annular rotary knife blade in the disposable blade support assembly, the blade retainer structure including a one piece annular retainer assembly;

FIG. 22 is a schematic sectional view of the blade support assembly, the annular rotary knife blade, and the one piece blade retainer structure of FIG. 21;

FIG. 23 is a schematic, enlarged sectional view of a portion of the blade support assembly, annular rotary knife blade, and the one piece blade retainer structure of FIG. 22;

FIG. 25 is a schematic sectional view of the blade support assembly, the annular rotary knife blade, and the two piece blade retainer structure of FIG. 23;

FIG. 26 is a schematic, enlarged sectional view of a portion of the blade support assembly, annular rotary knife blade, and the one two piece blade retainer structure of FIG. 25;

DETAILED DESCRIPTION

Figure 1:
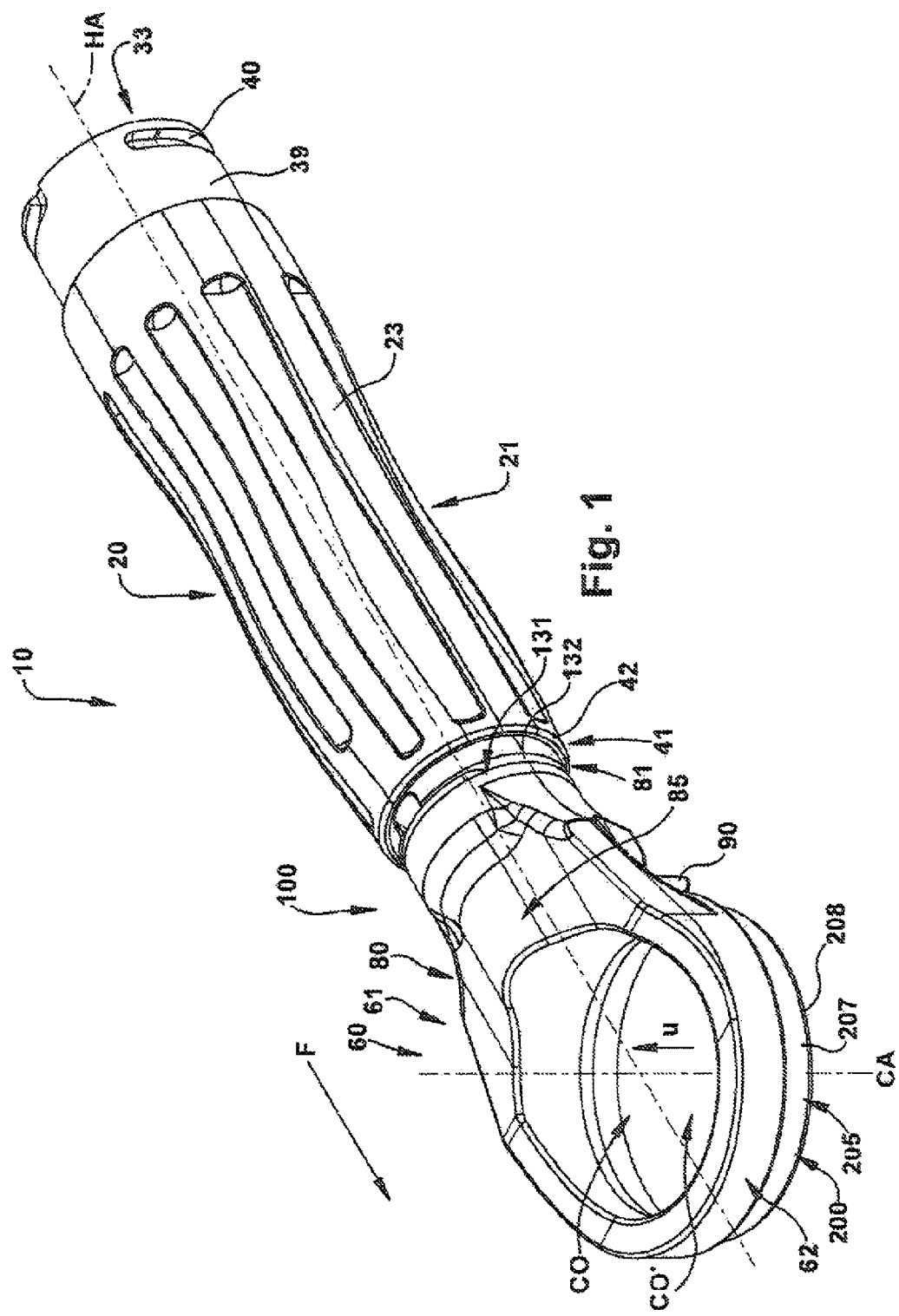
FIG. 1 is a schematic perspective view of an exemplary embodiment of a power operated rotary knife of the present disclosure including a first handle attachment structure exemplary embodiment for releasably coupling a disposable blade support assembly to a reusable handle assembly.
Figure 2:
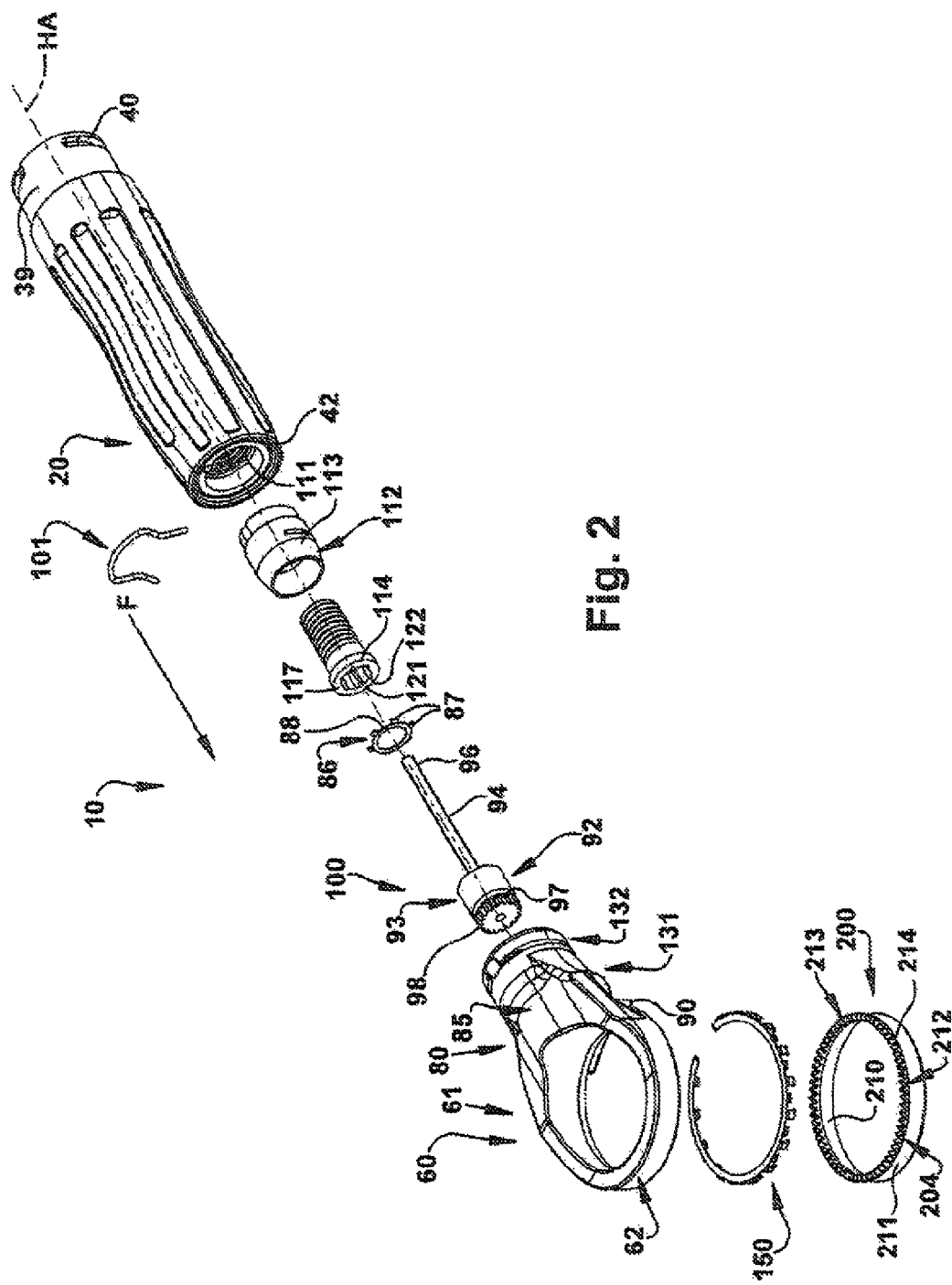
FIG. 2 is a schematic exploded perspective view of the power operated rotary knife of FIG. 1.

The present disclosure relates to a method and apparatus for using a power operated rotary knife to remove and/or recover tissue from a donor in connection with tissue recovery operations, including, but not limited to, bone debriding, full thickness skin debriding, and/or tendon/ligament recovery operations/processes (all such tissue removal/recovery operations will generally be referred to herein as "removing tissue", "recovering tissue", "debriding tissue" or "tissue debriding"). More specifically the present disclosure relates to a power operated rotary knife having a reusable handle assembly and disposable blade support assembly, wherein upon completion of tissue removal/recovery/debriding operations on a donor, the used blade support assembly is removed from the handle assembly and disposed of, the handle assembly is autoclaved/sterilized and a new, sterilized blade support assembly is affixed to the handle assembly prior to using the knife for a subsequent harvesting operation a new donor. Advantageously, the handle assembly is configured to be easy to assemble and disassemble and is fabricated of materials that are durable and able to withstand repeated autoclave/sterilization cycles. Also, advantageously, the main body of the blade support assembly, in one exemplary embodiment, is fabricated of PPS (polyphenylene sulfide resin), a plastic material that is lightweight, strong, resistant to chemicals, suitable for injection molding and is relatively inexpensive.

An exemplary embodiment of a power operated rotary knife of the present disclosure is shown generally at 10 in FIGS. 1-6. The power rotary knife 10 includes a reusable handle assembly 20, a disposable blade support assembly 60, an attachment assembly 100 to releasably attach the handle assembly 20 to the blade support assembly 60 and a blade retainer structure 150 to secure an annular rotary knife blade 200 for rotation in a blade housing portion 62 of the blade support assembly 60. The blade support assembly 60 includes an integral molded main body 61 which includes the blade housing portion 62 and a head portion 80. In one exemplary embodiment, the one-piece main body 61 is fabricated of PPS or other material known to have comparable properties. The head portion 80, among other things, supports a drive gear mechanism 92 which rotates the blade 200 within the blade housing portion 62.

The blade 200 is supported by the blade housing portion 61 for rotation about a central axis of rotation CA (FIGS. 3 & 4). The central axis of rotation CA of the blade 200 is substantially congruent with a central axis of the blade housing portion 62. The handle assembly 20 extends away from the blade support assembly 60 along a handle axis HA (FIG. 1) that is substantially orthogonal to the blade central axis CA, allowing an operator of the knife 10 to wield the knife with one hand. As used herein, axial, upper and lower shall mean movement or a dimension in a direction generally along or parallel to an extent of the central axis CA. Forward or distal shall mean in a direction generally along a direction labeled F in FIG. 1, the direction F being generally parallel to or along the handle axis HA. Rearward or proximal shall mean generally in a direction opposite of direction F.

Advantageously, the present disclosure contemplates a number of exemplary embodiments of the attachment assembly 100 and a number of exemplary embodiments of the blade retainer structure 150, each of the attachment assembly embodiments capable of being matched interchangeably with each of the blade retainer structure embodiments so as to provide maximum flexibility for the rotary knife design of the present disclosure. Additionally, the present disclosure contemplates at least two different drive assemblies, an air motor embodiment and a flexible drive shaft embodiment to provide motive power to rotate the blade 200 within the disposable blade support assembly 60.

Handle Assembly 20

Figure 5:
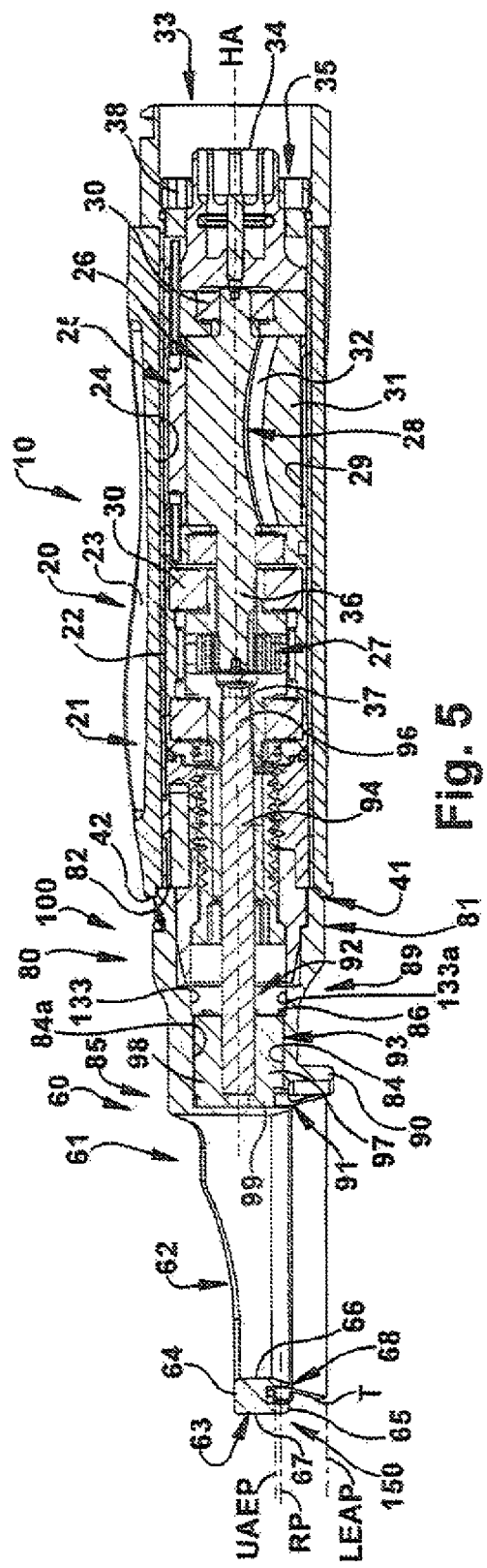
FIG. 5 is a schematic longitudinal sectional view of the power operated rotary knife of FIG. 1.

As can best be seen in FIG. 5, the handle assembly 20 includes an elongated handle 21 extending along the handle axis HA. The handle 21 includes a handle assembly inner sleeve 22 and an outer hand grip 23. The outer hand grip 23 is fabricated of a waterproof, resilient material and is contoured for easy gripping. In one exemplary embodiment the inner sleeve 22 is fabricated of stainless steel and the outer hand grip 23 is a softer, thermal plastic rubber that is overmolded onto the sleeve. Alternately, the inner sleeve 22 and the hand grip 23 may be fabricated as a one piece, high temperature plastic member. The handle assembly inner sleeve 22 defines a longitudinal throughbore 24. Supported in the handle longitudinal throughbore 24 is a drive assembly 25 including a vane-type air or pneumatic motor 26 and a planetary gear reduction unit 27. The motor 26 includes a rotor 28 mounted eccentrically within a bore defined by a motor body 29. The rotor 28 is supported for rotation by a pair of ball bearings 30 within the motor body 29.

A plurality of vanes 31 are supported for radial inward and outward movement in respective slots 32 formed in the outer surface of the rotor 28. High pressure air is communicated via an air hose (not shown) coupled to a proximal end 33 of the handle assembly 20 and directed into the motor body 29 through an air inlet 34. The air is routed through the motor body 29 and directed against the plurality of vanes 31 to rotate the rotor 28 as is conventional in vane-type air motors. Exhaust air exits the motor body 29 via an air outlet 35 that surrounds the air inlet 34. The rotor includes an output shaft 36 coupled to the planetary gear reduction unit 27. The torque at the rotor output shaft 36 is a product of air pressure, vane area exposed between an outside surface of the rotor and the motor body bore, and a moment arm of the vanes.

The planetary gear reduction unit 27 serves to convert the high rotational speed of the rotor shaft 36 to a drive coupling 37 that rotates at a lower speed but a higher torque output than the rotor shaft. The planetary gear reduction unit 27 and the pneumatic motor 26 are secured within the throughbore 24 of the handle assembly inner sleeve 22 by a retaining nut 38 that bears against the motor body 29. The drive coupling 37 of the planetary gear reduction unit 27 receives a proximal end portion 96 of a driven shaft 94 of the drive gear mechanism 92 which, in one exemplary embodiment, is a pinion gear assembly 93. The drive gear mechanism 92 is part of the disposable blade support assembly 60.

As can best be seen in FIGS. 3 & 4, a cylindrical proximal end 39 of the handle assembly inner sleeve 22 includes a groove 40 in an outer surface of the sleeve. The groove accepts a twist bayonet lock of an air hose (not shown) which provides air to the pneumatic motor 26. A foot pedal valve is coupled to the air hose to provide the operator with the ability to activate the knife 10, i.e., supply air to the motor 26 thereby causing the annular rotary knife blade 200 to rotate at a high rotational speed (on the order of 1,500-2,000 RPM) within the blade housing portion 62 of the disposable blade support assembly 60. Alternately, an actuation valve (not shown) may be mounted to the proximal end 39 in which case the knife 10 is actuated by a lever (not shown) pivotally coupled to the handle assembly 20. The motor 26 is actuated when the hand grip 23 is grasped by the operator and the lever is pivoted toward the hand grip and is turned off when the lever is released by the operator.

Figure 7:
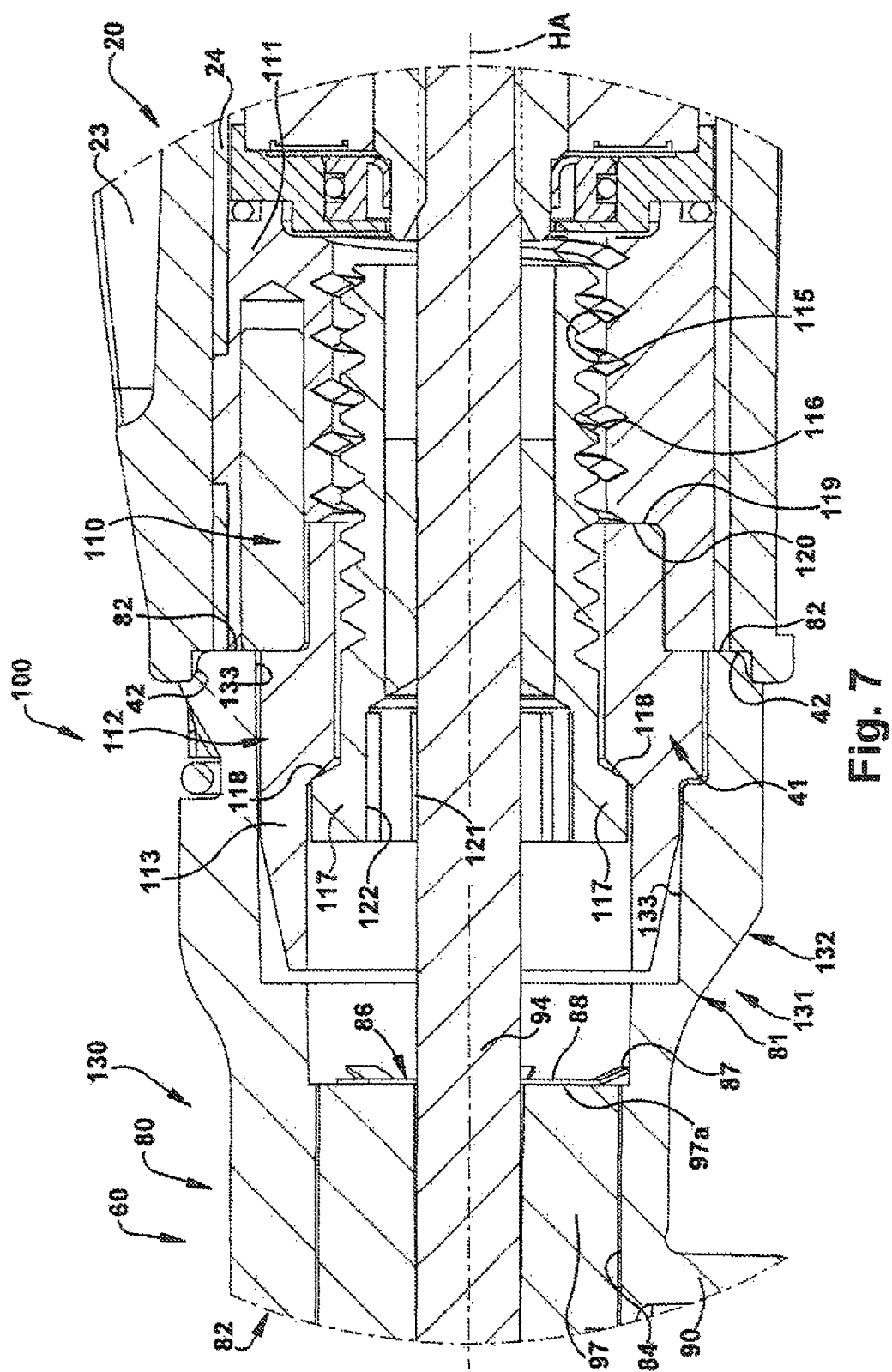
FIG. 7 is a schematic longitudinal sectional view of a portion of the power operated rotary knife of FIG. 1 showing the first handle attachment structure embodiment.
Figure 12:
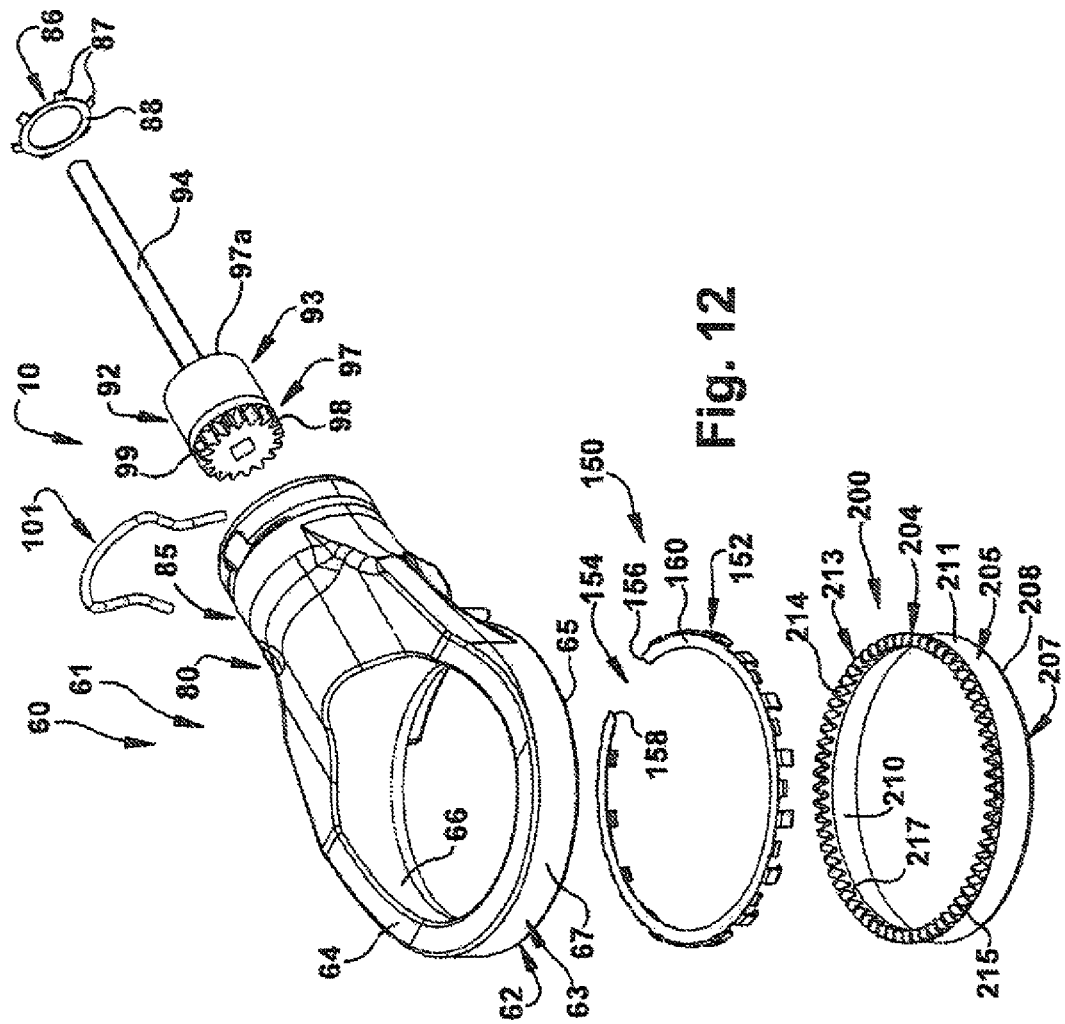
FIG. 12 is a schematic perspective view of a portion of the power operated rotary knife of FIG. 10 showing a disposable blade support assembly and a first blade retainer structure exemplary embodiment to retain an annular rotary knife blade in the disposable blade support assembly, the blade retainer structure including a one piece, tabbed retainer.

As can best be seen in FIG. 7, the handle assembly 20 also includes an attachment structure 110 supported within a forward or distal end portion 41 of the handle assembly. While the handle assembly attachment structure 110 is part of the handle assembly 20, it is also a component of the attachment assembly 100. The handle assembly attachment assembly 110 engages an attachment structure 130 of the head portion 80 of the disposable blade support assembly 60 to releasably attach the blade support assembly 60 to the handle assembly 20. The attachment assembly 100, including the handle assembly attachment structure 110 and the head portion attachment structure 130, facilitate removing and disposal of the disposable blade support assembly 60 from the reusable handle assembly 20, for example, subsequent to completion of tissue debriding on a given donor. The used blade support assembly advantageously is replaced with a new, sterilized blade support assembly prior to a subsequent tissue debriding session on a new donor. In the meantime, the handle assembly 20 is configured to be easily disassembled and sterile, such that it is sterilized prior to attachment of a new, sterilized blade support assembly. In one exemplary embodiment, the handle assembly attachment structure 110 is plugged and the proximal end 33 of the handle assembly 20 is covered with a cap to protect the air motor 26 from damage during the sterilization process.

The handle assembly attachment structure 110 includes a coupling 111 affixed to the handle assembly inner sleeve 22, a cylindrical collar 112 that includes an interface element such as interface projection 113 that projects distally (in a direction F) from a front wall 42 defined by the handle assembly 22, and a threaded retainer 114 which secures the collar 112 against the coupling 111. The collar interface projection 113 engages the blade support assembly head portion attachment structure 130. In one exemplary embodiment, the head portion attachment structure 130 includes a proximal/rearward cylindrical interface region 131 in the form of a socket 132. The socket 132 defines a generally cylindrical opening 133. The interface projection 113 matingly engages and fits within the cylindrical opening 133 of the socket 132.

As can best be seen in FIG. 7, the coupling 111 includes internal threads 115 that receive mating external threads 116 of the threaded retainer 114. The threaded retainer 114 includes a radially outward stepped distal end portion 117 which, when the retainer 114 is threaded into the coupling 111, bears against an internal shoulder 118 of the collar 112. As the threaded retainer 114 is threaded into the coupling 111, the retainer end portion 117 engages and bears against the collar internal shoulder 118 to force a stepped rearward end portion 119 of the collar 112 against a corresponding stepped forward end 120 of the coupling 111 to rigidly secure the collar 112 with respect to the handle assembly 20. Advantageously, the retainer 114 includes a hex shaped central opening 121 at a forward end 122 of the retainer 114 to allow for easy assembly/disassembly of the retainer 114 and the collar 112 from the handle assembly 20 using a conventional hex shaped drive tool.

Blade Support Assembly 60

The blade support assembly 60 includes the blade housing portion 62 and a head portion 80 which are part of a unitary main body 61. The blade housing portion 62 supports the annular rotary knife blade 200 for rotation, while the head portion 80 supports the drive gear mechanism 92. The drive gear mechanism 92 is driven by the drive assembly 25 of the handle assembly 20 and, in turn, rotates the rotary knife blade 200, as it is supported within the blade housing portion 62. The head portion 80 also includes the attachment structure 130. While the head portion attachment structure 130 is part of the head portion 80, it is also a component of the attachment assembly 100. The head portion attachment structure 130 engages the handle assembly attachment structure 110 to releasably attach the blade support assembly 60 to the handle assembly 20.

Head Portion 80

The head portion 80 of the blade support assembly 60 includes the attachment structure 130 formed in the generally cylindrical interface region 131 at a rearward/proximal end 81 of the head portion 80. The interface region 131 includes the socket 132 which defines the cylindrical opening 133 (FIG. 7) that extends substantially along the handle axis HA and receives the interface projection 113 of the handle assembly attachment structure 110. The rearward end 81 of the head portion includes a stepped proximal or rear wall 82. As can best be seen in FIG. 7, when the handle assembly 20 and the blade support assembly 60 are properly and fully engaged, the stepped rear wall 82 of the head portion interface region 131 abuts the front wall 42 of the handle assembly.

The blade support assembly 60 further includes the drive gear mechanism 92 rotatably supported within the head portion 80. The drive gear mechanism 92 includes a pinion gear 97 and an integral driven shaft 94. In one exemplary embodiment, the pinion gear 97 is comprised of temperature-resistant plastic material such as polyetheretherketone (PEEK) or some other suitable material, while the driven shaft 94 is comprised of metal or some other suitable material. The pinion gear 97 includes a plurality of gear teeth 98 that mesh with a plurality of gear teeth 214 of the rotary knife blade 200 to rotate the blade 200. The rearward end portion 96 of the driven shaft 94 is coupled to and rotatably driven by the drive coupling 37 of the planetary gear reduction unit 27. This causes rotation of the pinion gear 97 and, in turn, rotates the blade 200.

The pinion gear 97 is supported for rotation in a cylindrical cavity 84 defined within a body region 85 the head portion 80. The cavity 84 is longitudinally aligned with the cylindrical opening 133 of the interface region 131, that is, aligned along the handle axis HA and slightly smaller in diameter than the interface region cylindrical opening 133. The cavity 84 is defined by a cylindrical wall 84a and is positioned in the head portion body region 85 such that a forward portion 99 (FIG. 5) of the gear teeth 98 of the pinion gear 97 engage and drive the corresponding gear teeth 214 of the annular rotary knife blade 200.

A retainer ring 86 is inserted into a distal end of the cylindrical opening 133, adjacent the cavity 84. The retainer ring 86 includes six resiliently deflectable tabs 87 (FIG. 2) projecting radially outwardly from an annular body 88. As can best be seen in FIG. 7), when the retainer ring 86 is inserted into the cylindrical opening 133. The retainer ring 86 is slightly oversized compared to the diameter of the cylindrical opening 133 such that the tabs 87 of the retainer ring 86 deform slightly against a wall 133a defining the cylindrical opening 133 to hold it securely in place within the cylindrical opening 133, adjacent the cavity 84. When in place in the cylindrical opening 133 adjacent the cavity 84, the annular body 88 of the retainer ring 86 bears against a back wall 97a of the pinion gear 97 to maintain the pinion gear in place within the cavity 84.

Figure 15:
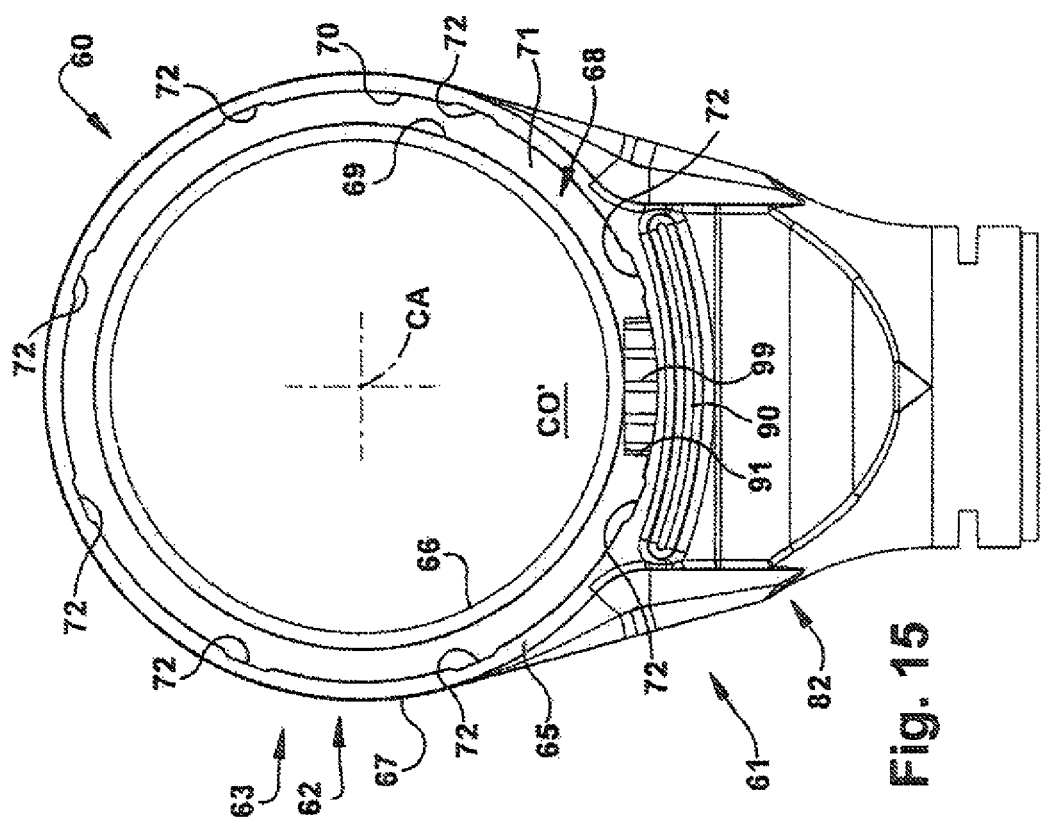
FIG. 15 is a schematic bottom plan view of the disposable blade support assembly of FIG. 12 with the annular rotary knife blade and the tabbed blade retainer structure removed to shown retaining notches in the blade housing portion to accept the tabbed blade retainer structure.

A lower portion of the body region 85 of the head portion 80 includes a radially inwardly tapered portion 89 and a radially downwardly extending finger guard 90 to reduce the changes of an operator's fingers slipping forward on the handle grip 23 and contacting the rotating blade 200. As can best be seen in FIG. 15, forward of the finger guard 90 is a pinion gear opening 91 in the body region 85 in communication with the pinion gear cavity 84. As can best be seen in FIGS. 5 and 15, the opening 91 provides clearance for engagement of the forward portion 99 of the plurality of gear teeth 98 of the gear pinion gear 97 with the plurality of gear teeth 214 of the rotary knife blade 200. As the pinion gear 97 is rotated about its axis of rotation, which is congruent with the driven shaft 94, the blade 200 is rotated about its central axis CA and is supported for rotation within a rotational plane RP (FIGS. 3, 5 & 19) defined by the blade housing portion 62 and the blade retainer structure 150.

Blade Housing Portion 61

The blade housing portion 62 comprises a generally annular shaped ring 63 that extends forward (in the direction F) from the head portion 80. As can best be seen in FIGS. 5 & 18, the annular ring 63 includes a top or upper wall 64, a bottom wall 65, an inner wall 66 and an outer wall 67. In regions extending away from the head portion 80, the annular ring 63 is generally rectangular in cross section. The bottom wall 65 of the annular ring 63 includes an annular groove or opening 68. The rectangular cross section of the annular ring 63 provides strength and rigidity to absorb the significant torque that is generated by an operator when, for example, forcing a distal tip T (FIGS. 3 & 5) of the blade 200 against a bone when debriding tissue from the bone. As can best be seen in FIG. 15, the groove 68 forms a complete circle, that is, subtends an angle of 360°, and extends axially upwardly from the bottom wall 65 of the ring 63. As can best be seen in FIGS. 16-20, the groove 68, when viewed in cross section, is generally an inverted U-shape and is defined by a radially inner wall 69, a radially spaced apart outer wall 70, and a top wall 71. In one exemplary embodiment, a radial distance from the central axis CA of the blade 200 and blade housing portion 62 of the disposable blade support assembly 60 to the outer wall 70 is approximately one inch. In the illustrated example embodiment of FIGS. 16-20, the radial distance from the central axis CA of the blade 200 and blade housing portion 62 of the disposable blade support assembly 60 to the outer wall 70 is approximately 1.039 inches and a radial distance across the annular groove is approximately 0.112 inch.

The annular groove 68 is sized to receive both an annular body support section 204 of the blade 200 and the blade retainer structure 150 which functions to permanently retain the blade in the groove and serves as a bearing structure for the blade as the blade rotates within the blade support assembly. In the region of the head portion 80, the upper wall 64 and the outer wall 67 transition or taper smoothly into the larger main body region 85 of the head portion 80. The groove 68 defined by the bottom wall 65 and the blade retainer structure 150 define the horizontal rotational plane RP of the knife blade 200, the rotational plane RP being substantially orthogonal to the central axis CA of the blade. The inner wall 66 of the blade housing portion 62 also defines an axially extending central opening CO' such that material, such as tissue, that is cut by the cutting edge 208 of the blade 200 flows in an upward direction U (FIGS. 1 & 3) upwardly through a central opening CO of the blade and also through the central opening CO' of the blade housing where it exits the rotary knife 10.

Blade 200

As can best be seen in FIG. 20, the blade 200 includes a first, upper axial end 201 and a second, lower axial end 202, spaced axially apart by an annular body 203. The rotatable annular body 203 includes the annular body support section 204 that extends downwardly from the upper axial end 201 and is generally cylindrical in configuration, that is, generally rectangular in cross section. The annular body 203 also includes a lower blade section 205 that extends downwardly and slightly radially inwardly from a lower, radially outer portion 206 of the annular body support section 204. A lower portion 207 of the blade section 205 adjacent the lower axial end 202 defines the cutting edge 208 of the blade 200.

Extending between the upper and lower axial ends 201, 202, respectively, the annular body 203 of the blade 200 is defined by an inner wall 210 and a radially spaced apart outer wall 211. An upper portion 212 of the annular body support section 204 defines a drive gear section 213 including a plurality of spaced apart gear teeth 214. The plurality of gear teeth 214 extend downwardly from the upper axial end 201 and further extend between and through the outer wall 211 and the inner wall 210. The outer wall 211 in the region of the annular body support section 204 defines the outermost radial surface of the blade 200. The plurality of spaced apart gear teeth 214 mesh with mating gear teeth 98 of a pinion gear 97 of the pinion gear assembly 93 to rotate the blade 200 in the blade housing portion 62.

A central axis of the rotatable annular body 203 is congruent with and the same as the blade central axis CA and, for simplicity, both the blade central axis and the annular body central axis shall be referenced herein as CA. The upper axial end 201 includes an upper surface of the plurality of gear teeth 214, while the lower axial end 202 includes a lower surface of the cutting edge 208 of the blade. As can be seen in FIGS. 5 & 18, the upper axial end 201 defines a generally planar surface UAEP and the lower axial end 202 defines a generally planar surface LAEP. The planes UAEP, LAEP are substantially parallel, substantially orthogonal to the blade/annular body central axis CA, and substantially parallel to the rotation plane RP of the blade 200. The inner wall 210 of the blade 200 defines the central opening CO of the blade and is angled such that material that is cut by the cutting edge 208 of the blade flows upwardly through and exits the blade. In one exemplary embodiment of the present disclosure, the diameter of the central opening CO at the lower axial end 202 of the blade 200 is approximately 1.997 inches, the diameter of the central opening CO at its largest diameter near the upper axial end 201 is approximately 1.872 inches, while the outer diameter of the blade at its largest diameter, which is near the upper axial end 201 is approximately 2.030 inches. In one exemplary embodiment, an axial height of the blade 200 measured from the upper axial end 201 to the lower axial end 202 is approximately 0.340 inches. The blade 200 may be fabricated of a hardenable grade of alloy steel or a hardenable grade of stainless steel, or other material known to have comparable properties.

Attachment Assembly 100

The attachment assembly 100 provides for a secure attachment between the blade support assembly 60 and the handle assembly 20 when the attachment assembly is engaged. The attachment assembly 100 also provides for quick and easy detachment of the blade support assembly 60 from the handle assembly 20 such that the blade support assembly 60 may be removed and discarded after, for example, completion of a tissue debriding session on a donor. After the handle assembly 20 is sterilized, the attachment structure 100 provides for easy and fast attachment of a new, sterilized blade support assembly 60 to the sterilized handle assembly 20.

The attachment assembly 100 includes the socket 132 of the head portion attachment structure 130 and the collar 112 of the handle assembly attachment structure 110. The interface element or projection 113 of the collar 112, which extends forward from the front wall 42 of the handle assembly interfits into the cylindrical opening 133 of the socket. As can best be seen in FIGS. 7 and 8, when the blade support assembly 60 is properly attached to the handle assembly 20, the stepped, rearward wall 82 of the head portion 80 bears against and matingly engages the corresponding stepped portion of the front wall 42 of the handle assembly 20.

Figure 6:
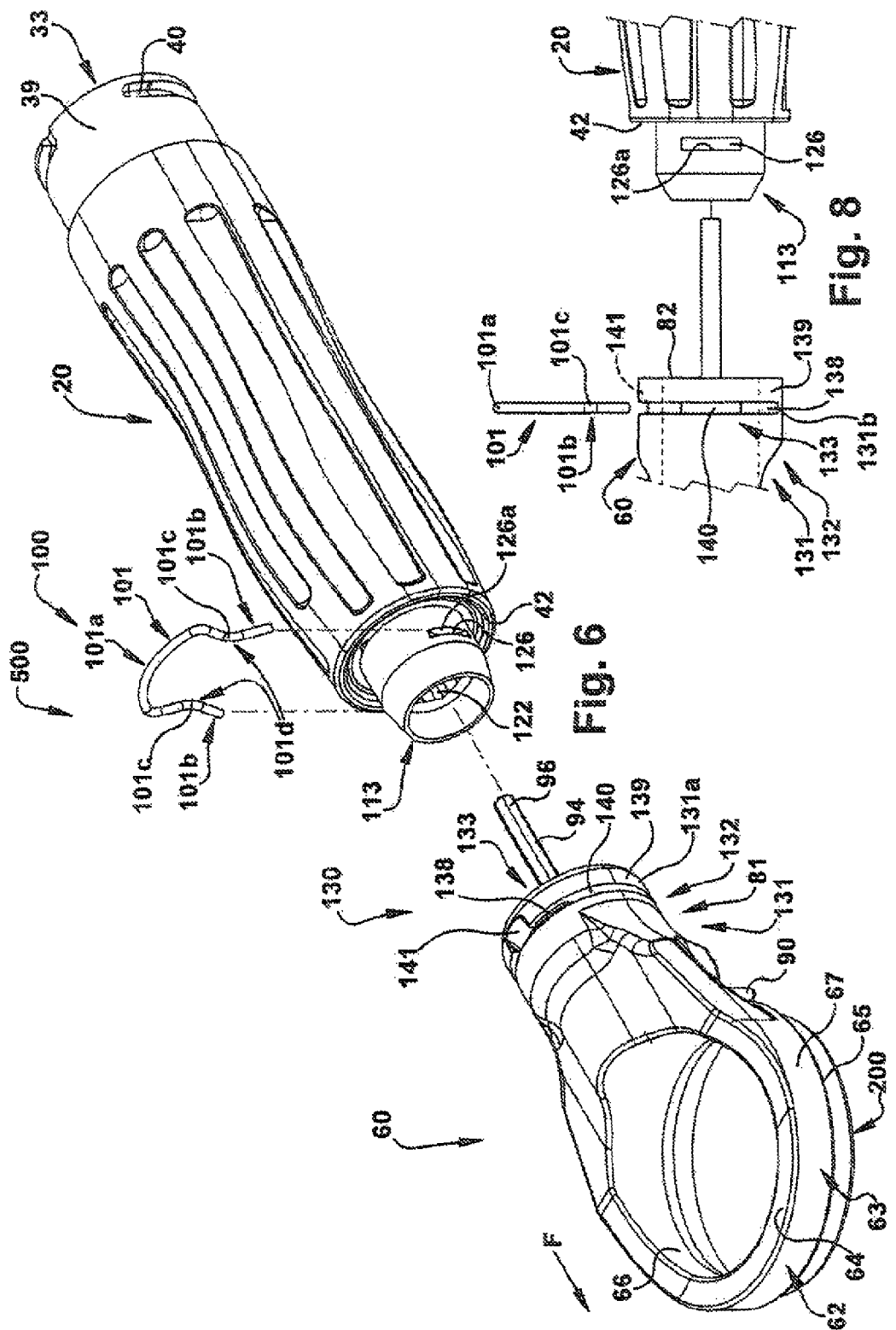
FIG. 6 is a schematic perspective view of the power operated rotary knife of FIG. 1 with the reusable handle assembly detached from the disposable blade support assembly to show the first handle attachment structure embodiment.

In one exemplary embodiment, the attachment assembly 100 utilizes a generally U-shaped retaining clip 101 to affix the blade support assembly 60 to the handle assembly 20. As is best seen in FIG. 6, the clip 101 includes a central portion 101*a* and two arms 101*b* extending from the central portion 101*a*. The two arms 101*b* each include a middle portion 101*c* which curve inwardly toward each other forming a narrow waist region 101*d*. The arm middle portions 101*c* defining the narrow waist region 101*d* are sized to snuggly fit into recessed portions 126 (one of which can be seen in FIGS. 6 and 8) formed on opposite sides of the interface projection 113 of the handle assembly 20.

An outer surface 131*a* of the cylindrical interface region 131 defining the socket 132 includes an annular groove 138. As can best be seen in FIG. 8, the annular groove 138 extends a majority of the way, but not entirely around the peripheral outer surface 131*a* of the cylindrical interface region 131. The annular groove 138 does not extend around a small, lower portion 131*b* (FIG. 8) of the outer surface 131*a* of the interface region 131. In opposite side regions of the annular groove 138, the groove extends completely through the wall of the socket 132 thereby forming a pair of spaced apart, slot-shaped openings 140 (one of which can be seen in FIGS. 6 and 8). The slot-shaped openings 140 are aligned with the recessed portions 126 of the interface region 113 when the blade support assembly 60 is attached to the handle assembly 20. An angled region 141 adjacent the annular groove 138 near the top of the outer surface 131*a* of the cylindrical interface region 131 is provided to facilitate insertion of a tool head, such as the head of a screwdriver to remove the retaining clip 101 when detachment of the blade support assembly 60 is desired.

When the interface projection 113 of the handle assembly 20 is longitudinally aligned with the cylindrical opening 133 defined by the socket 132 and the blade support assembly 60 is moved toward the handle assembly 20, the interface projection 113 fits within the opening 133 of the socket 132 and the slot-shaped openings 140 of the annular groove 138 are aligned with respective ones of the recessed portions 126 of the interface projection 113. The retaining clip 101 is then aligned with the annular groove 138 and pushed downward until the middle portion 101*a* is firmly seated in the groove 138. When the retaining clip 101 is fully inserted, the middle portions 101*c* of the arms 101*b* pass through the slot-shaped openings 140 of the annular groove 138 and snap fit into the respective recessed portions 126 of the interface projection 113 to secure the blade support assembly 60 to the handle assembly 20.

The retaining clip 101, which fits snuggly in the annular groove 138, bears against forward facing surfaces 126a bounding the recessed portions 126 of the interface projection 113 to prevent the detachment of the blade support assembly 60 from the handle assembly 20. In this embodiment, the retaining clip 101 is a retainer that attaches the blade support assembly 60 and the handle assembly 20. The annular groove 138 of the socket 132 is a retainer receiver that receives the retainer (retaining clip 101). The forward facing surfaces 126a of the interface projection 113 bounding the recessed portions 126 define bearing surfaces that bear against the retainer (retaining clip 101) to prevent detachment of the handle assembly 20 and the blade support assembly 60.

For removal of the disposable blade support assembly 60 from the handle assembly 20, the operator inserts a suitable tool, such as the head of a screwdriver, into the angled region 141 and pries the retaining clip 101 up and out of the annular groove 138. Once the retainer clip 101 is removed, the operator then pulls the blade support assembly 60 in the forward direction F with one hand while holding the handle assembly 20 stationary with his or her other hand until the interface projection 113 is disengaged from the socket 132.

Second Exemplary Embodiment of Attachment Assembly 400

FIGS. 9 and 10 schematically depict a rotary knife 300 of the present disclosure including a second exemplary embodiment of an attachment assembly 400 to detachably affix a disposable blade support assembly 360 to a reusable handle assembly 320. For simplicity, only the differences from the prior embodiment will be described herein, it being understood that the overall configuration and operation of the rotary knife 300 of the present embodiment is substantially the same as the rotary knife 10 of the first embodiment.

In this embodiment, the rotary knife 300 includes the reusable handle assembly 320 and the disposable blade support assembly 360. The attachment assembly 400 provides for secure attachment between the blade support assembly 360 and the handle assembly 320 when the attachment assembly is engaged, while at the same time provides for quick and easy detachment of the blade support assembly 360 from the handle assembly 320 when the attachment assembly is disengaged.

In the present embodiment, instead of using a retaining clip 101, as was the case in the first embodiment, in the present embodiment the attachment assembly 400 utilizes an O-ring 401 to affix the blade support assembly 360 to the handle assembly 320. The interface projection 413 of the handle assembly 320 includes four radial projections or bosses 424 extending from an outer surface 425 of the interface projection. A cylindrical interface region 431 defining a socket 432 includes an annular groove 438 in an outer surface 439 of the cylindrical interface region and four axially extending passageways 440 (two of which can be seen in FIG. 9) extending between the stepped rear wall 382 of the head portion 380 and the annular groove 438. The O-ring 401 is sized to snuggly fit into the annular groove 438. The cylindrical socket 432 further includes four recesses 441 (two of which can be seen in FIG. 10) just forward of the annular groove 438, the four recesses 441 are sized to receive and seat the four bosses 424.

Prior to attachment, the O-ring 401 is stretched and positioned on the head portion socket 432 just forward or distally of the annular groove 438. The blade support assembly 360 and the handle assembly 320 are aligned such that the interface projection 413 of the handle assembly 320 is longitudinally aligned with the cylindrical opening 433 defined by the socket 432. As the blade support assembly 360 is moved toward the handle assembly 320, the bosses 424 of the interface projection 413 pass through respective passageways of the four passageways 440 of the interface region socket 432 and are seated in respective recesses of the four recesses 441.

The attachment assembly 400 is engaged by sliding the stretched O-ring 401 from its position on the head portion 380 into the annular groove 438. The O-ring 401, which is sized to fit tightly in the annular groove 438, bears against rearward facing surfaces 424a of the bosses 424 to prevent the detachment of the blade support assembly 360 from the handle assembly 320. In this embodiment, the O-ring 401 is a retainer that attaches the blade support assembly 360 and the handle assembly 320. The annular groove 438 of the socket 432 is a retainer receiver that receives the retainer (O-ring 401). The rearward facing surface 424a of the bosses 424 of the interface projection 413 define bearing surfaces that bear against the retainer (O-ring 401) to prevent detachment of the handle assembly 320 and the blade support assembly 360.

For disengagement of the attachment assembly 400, that is, removal of the disposable blade support assembly 360 from the handle assembly 320, the operator cuts the O-ring 401 with a suitable cutting tool, such as a knife. Once the O-ring 401 is removed, the operator then pulls the blade support assembly 360 in the forward direction F with one hand while holding the handle assembly 320 stationary with his or her other hand until the interface projection 413 is disengaged from the socket 432.

Third Exemplary Embodiment of Attachment Assembly 600

FIG. 11 schematically depicts a rotary knife 500 of the present disclosure including a third exemplary embodiment of an attachment assembly 600 to detachably affix a disposable blade support assembly 560 to a reusable handle assembly 520. For simplicity, only the differences from the prior embodiments will be described herein, it being understood that the overall configuration and operation of the rotary knife 500 of the present embodiment is substantially the same as the rotary knife 10 of the first embodiment.

In this embodiment, the rotary knife 500 includes the reusable handle assembly 520 and the disposable blade support assembly 560. The attachment assembly 600 provides for secure attachment between the blade support assembly 560 and the handle assembly 520 when the attachment assembly is engaged, while at the same time provides for quick and easy detachment of the blade support assembly 560 from the handle assembly 520 when the attachment assembly is disengaged.

In the present embodiment, instead of using a retaining clip fastener 101, as was the case in the first embodiment, a threaded fastener 601 such as a threaded screw 601 is used to releasably engage the blade support assembly 560 and the handle assembly 520. The threaded screw 601 includes a threaded stem 602 and an enlarged slotted head 603. A cylindrical interface region 631 of the head portion 580 of the blade support assembly 560 defines a socket 632. The interface region 631 also includes a longitudinally extending slotted opening 634 and a countersink area 635 formed in an outer surface 621a of the interface region and centered about a forward end portion 636 of the slotted opening 634. The interface projection 613 of the handle assembly attachment structure 610 includes a threaded opening 623 that is aligned with the forward or distal end portion 636 of the slotted opening 634 of the interface region 631. When the blade support assembly 560 is properly attached to the handle assembly 520, the forward end portion 636 of the slotted opening 634 of the socket 632 is aligned with the threaded opening 623 of the interface projection 613.

To engage the attachment assembly 600, a two step process is used. First, the interface projection 613 of the handle assembly 520 is longitudinally aligned with the cylindrical opening 633 of the socket 632 of the blade support assembly 560, that is, along the handle axis HA, and the two parts are brought together such that the threaded opening 623 of the interface projection 613 is aligned radially with the forward end portion 636 of the slotted opening 634 (the alignment shown in FIG. 11) and the front wall 542 of the handle assembly 520 abuts the rearward wall 631b of the cylindrical interface region 631.

Second, after the handle assembly 520 and the blade support assembly 560 are properly and fully engaged, the threaded fastener 601 is used to secure the blade support assembly 560 in the attached position with respect to the handle assembly 520. The threaded stem or body 602 of the threaded fastener 601 passes though the forward end portion 636 of the slotted opening 634 and threads into the threaded opening 623 of the interface projection 613. When the fastener 601 is threaded into the opening 623, the enlarged head 603 of the threaded fastener is snuggly received into the countersink region 635 and bears against the portions of socket 632 forming the countersink region 635. Particularly, rearward shoulder portions 637 of the socket 632 that form a side wall of the countersink region 635 adjacent the slotted opening 634 bear against the fastener enlarged head 603 to prevent relative movement of the blade support assembly 560 in a forward direction with respect to the handle assembly 520 when the fastener 600 is threaded into the threaded opening 623 of the interface projection 613. When the handle assembly 520 and the blade support assembly 560 are properly and fully engaged and the fastener 601 is threaded into the threaded opening 623 of the interface projection, the attachment assembly 600 is engaged, that is the disposable blade support assembly 560 is affixed to the handle assembly 520.

In essence, the threaded fastener 601 is a retainer that attaches the blade support assembly 560 and the handle assembly 520 and the threaded opening 623 of the interface projection 613 is a retainer receiver that receives the retainer (threaded fastener 601). The rearward shoulder portions 637 of the socket 632 defining the side wall of the countersink region 635 adjacent the slotted opening 634 define bearing surfaces to bear against the retainer (threaded fastener 601) to prevent detachment of the handle assembly 520 and the blade support assembly 560.

To disengage the attachment assembly 600, that is, to remove the blade support assembly 560 from the handle assembly 520, the operator simply uses a screwdriver to remove the threaded fastener 601 from the threaded opening 623 of the interface projection 613. Once the threaded fastener 601 is removed, the operator then pulls the blade support assembly 560 in the forward direction F with one hand while holding the handle assembly 520 stationary with his or her other hand until the interface projection 613 is disengaged from the socket 632. This two step process completes the detachment of the blade support assembly 560 from the handle assembly 520, that is, the attachment assembly is disengaged.

Blade Retainer Structure 150

FIGS. 12-20 schematically depict the rotary knife 10 of the present disclosure and, more specifically, schematically depict a first exemplary embodiment of the blade retainer structure 150 of the present disclosure. The rotary knife 10 depicted in FIGS. 12-20 actually includes the first attachment assembly 100 discussed above. However, as previously mentioned, any of the attachment assemblies 100, 400, 600 may be used interchangeably. As the focus in this section is on the blade retainer structure 150, not the specifics of the attachment assembly, for simplicity, the rotary knife and components will be referred to in terms of the reference numbers used in connection with the first embodiment discussed previously.

The blade retainer structure 150 retains and permits rotation of the annular rotary knife blade 200 within the annular groove 68 of the blade housing portion 62 of the disposable blade support assembly 60. The blade retainer structure 150, in the first exemplary embodiment, includes a one piece retainer 152. The retainer 152 may be fabricated of a resilient material, such as, for example, stainless steel spring material. The retainer 152 functions to both secure the blade annular body support section 204 in the blade housing annular groove 68 and to provide a bearing surface for rotation of the blade 200 about the blade central axis CA and along the blade rotational plane RP. As can best be seen in FIGS. 13 & 14, the retainer 152 does not form a complete circle or annulus. Rather, the retainer 152 includes defines a cut out region 154 between end portions 156, 158. The cut out region 154 of the retainer 152 provides clearance for the teeth 98 of the pinion gear 97, the pinion gear 97 being supported for rotation in the pinion gear opening 91 of the main body region 85 of the head portion 80.

The retainer 152 includes an upper wall 160 which extends horizontally and is substantially planar. As can be seen in FIGS. 18-20, there is a small clearance region between the retainer upper wall 160 and the top wall 71 of the annular groove 68. The clearance region allows for some travel of the retainer 152 when it is inserted in the groove 68 and to compensate for some limited non-uniformity or puckering of the retainer upper wall 160 when the retainer is inserted into the groove. The retainer 152 additionally includes a plurality of short, downwardly extending tabs 162 (FIG. 18), a plurality of angled locating/support tabs 164 (FIG. 20), and a plurality of L-shaped bearing legs 166 (FIG. 19), all extending from a radially outer peripheral region 168 of the retainer upper wall 160. The retainer 152 is first affixed to the blade 200, then the blade & retainer assembly 250 is inserted into the annular groove 68 and, when, properly seated in the annular groove, the blade & retainer assembly 250 becomes permanently affixed to the blade housing portion 62.

The L-shaped bearing legs 166 of the retainer 152 hold the blade 200 and provide a bearing surface for rotation of the blade 200 with respect to the retainer 152 and the blade housing portion 62. As can best be seen in FIG. 19, an inner surface 166a of a vertical portion 166b of the legs 166 extends along and provides a bearing surface for a vertical portion 215 of the outer wall 211 of the annular body support section 204 of the blade 200. Additionally, an upper surface 166c of a short horizontal portion 166d of the legs 166 extends along and provides a bearing surface for a radially outer horizontal portion 216 (FIG. 17) of the outer wall 211 of the annular body support section 204 of the blade 200. Thus, the L-shaped bearing legs 166 of the retainer 152 provide both vertical and horizontal bearing surfaces for the body support section 204 of the blade 200. In one exemplary embodiment, as can be seen in FIG. 14, there are fourteen L-shaped bearing legs 166.

A lower surface 160a of the upper wall 160 of the retainer 152 also serves as a horizontal bearing surface, bearing against the first, upper axial end 201 of the blade 200. The radial inner wall 69 defining the annular groove 68 also serves as a vertical bearing surface, bearing against a vertical portion 217 of the inner wall 210 of the annular body support section 204 of the blade 200.

It should be appreciated that not all of the mating bearing surfaces of the blade 200, the retainer 152 and the radial inner wall 69 of the annular groove 68, as described above, are in contact at any given time because there are necessarily running clearances between the blade, the retainer and the annular groove which allow the blade to rotate relatively freely within a region defined by the retainer 152 and the inner wall 69 of the blade housing annular groove 68. These running clearances cause the blade 200 to act somewhat akin to a teeter-totter within the blade housing retainer 152 and the annular groove 68, that is, as one region of the blade is pivoted or moved upwardly within the retainer and annular groove during a cutting or trimming operation in a bone debriding process, the diametrically opposite portion of the blade (180° away) is pivoted or moved downwardly within the retainer and annular groove. Accordingly, the mating bearing surfaces in contact at a specific location of the blade-retainer annular groove interface will change and, at any given time, will be determined by the forces applied during use of the rotary knife.

The blade retainer structure 150 also includes a plurality of locating recesses or notches 72 formed the outer wall 70 of the annular groove 68. As can best be seen in FIG. 15, in one exemplary embodiment, there are eight locating notches 72 spaced apart radially along the outer wall 70. In one embodiment, the notches 72 have a radial length of approximately 0.125 inches. In the retainer 152, the number of locating/support tabs 164 matches the number of locating notches 72. The locating/support tabs 164 are angled downwardly at an angle of approximately 15-30° with respect to the horizontal, planar upper wall 160 of the retainer 152.

When the blade & retainer assembly 250 (FIG. 13) is inserted into the annular groove 68, the eight horizontally extending locating/support tabs 164 extend into respective ones of the locating notches 69 thereby orienting the blade and retainer such that the pinion clearance region 154 of the retainer 152 is properly aligned with the pinion gear opening 91 at the bottom of the head portion 80 that provides clearing for the pinion gear-blade gear interface. Additionally, the radial distance of the retainer upper wall 160 and a length and angle of the locating/support tabs 164 are selected such that when the blade & retainer assembly 250 is inserted into the annular groove 68, the locating/support tabs 164 are forced to flex radially inwardly. As best seen in FIG. 20, distal ends 164a of each of the locating/support tabs 164 bear against and bite into portions of the outer wall 70 defining the locating notches 72 thereby providing an interference fit between the retainer 152 and the blade housing portion 62 of the blade support assembly 60.

Additionally, because of the interference fit between the locating/support tabs 164 of the retainer 152 and the outer wall 70 defining a portion of the annular groove 68 of the blade housing portion 62, a radially inner peripheral region 169 of the upper wall 160 is forced against the inner wall 69 defining the annular groove 68. Recall that the blade support assembly 60, in one preferred embodiment, is fabricated via molding a plastic material, thus, the retainer 152, being spring steel, is a relatively harder material than the blade support assembly 60. Consequently, the distal ends 164a of the tabs 164 bite or dig into the softer material of the outer wall 70 generating an interference fit. Further, the interference fit is permanent because attempting to remove the retainer 152 from the annular groove 68 would likely distort and bend the retainer to a condition where it would no longer be usable as a bearing support for the blade 200. The combination of the tension of the retainer upper wall 160 against the inner wall 69 and the locating/support tabs 164 bearing against and/or biting into the portions of the outer wall 60 defining the locating notches 72, the blade & retainer assembly 250 are permanently locked into place and are prevented from coming out of the annular groove 68. The retainer 152 is stationary with respect to the annular groove 68 and the blade housing portion 62, while the blade 200 is supported for rotation within the annular groove 68.

The plurality of short, downwardly extending tabs or stub tabs 162 (FIG. 18) of the retainer 152 bear against the outer wall 70 defining the annular groove 68 and provide additional stability and rigidity to the retainer and contribute to maintaining the blade & retainer assembly 250 properly seated in the annular groove 68. In one exemplary embodiment, as can be seen in FIG. 14, the number of short, downwardly extending tabs 162 is seven.

Second Exemplary Embodiment of Blade Retainer Structure 850

FIGS. 21-23 schematically depict a rotary knife 700 of the present disclosure including a second exemplary embodiment of a blade retainer structure 850 that retains and permits rotation of an annular rotary knife blade 900 within an annular groove 768 of the blade housing portion 762 of the disposable blade support assembly 760. For simplicity, only the differences from the prior embodiment will be described herein, it being understood that the overall configuration and operation of the rotary knife 700 of the present embodiment is substantially the same as the rotary knife 10 of the first embodiment.

In this embodiment, the rotary knife 700 includes the reusable handle assembly 720 and the disposable blade support assembly 760. The blade retainer structure 850, in the second exemplary embodiment, includes a one piece retainer 870. The retainer 870 may be fabricated of a resilient material, such as, for example, a durable plastic material such as PPS, previously discussed. The retainer 870 functions to both secure the blade annular body support section 904 in the blade housing annular groove 768 and to provide a bearing surface for rotation of the blade 900 about the blade central axis CA and along the blade rotational plane RP.

As can best be seen in FIG. 23, when viewed in cross section, the retainer is basically an inverted T-shape and includes a horizontal base 872 and an upright 874 extending vertically from a central portion of the base 872. Looking at FIG. 21, the base 872 of the retainer 870 forms a complete circle or, more specifically, an annulus. The upright 874 is also continuous and forms a complete circle, but includes a cut out region 876 (FIG. 21) that, upon insertion of the blade & retainer assembly 950 into the annular groove 768 of the blade housing portion 762, is aligned with the pinion gear clearance opening 791 of the main body region 785 of the head portion 780.

The blade & retainer assembly 950 is permanently affixed in the blade housing portion annular groove 768. First, the blade 900 is placed or positioned on (but not bonded) the blade retainer structure 850, namely, the retainer 870. Specifically, as can best be seen in FIG. 23, a portion of an inner wall 878 of the upright 874 is in contact with a vertical portion 915 of an outer wall 911 of the annular body support section 904 of the blade 900 and a portion of an inner, upper surface 880 of the base 872 is in contact with a radially outer horizontal portion 916 of the outer wall 911 of the annular body support section 904 of the blade.

After the blade 900 is placed on the retainer 870 as described above, the assembly 950 is then inserted and seated into the annular groove 768 of the blade housing portion 762 of the disposable blade support assembly 760. As best seen in FIG. 23, when the blade & retainer assembly 950 is inserted and seated into the annular groove 768, an outer wall 882 of the upright 874 of the retainer 870 is in contact with an outer wall 767 defining the annular groove 768, an upper surface 884 of the upright 874 is in contact with a top wall 771 defining the annular groove 768, and an outer, upper surface 886 of the base 872 is in contact with a portion 888 of the bottom wall 765 of the annular ring 763 of the blade housing portion 762. At least some of the contacting portions of the retainer 870 and the blade housing portion 762 are then permanently affixed via adhesive or fusing. In one exemplary embodiment, adhesive is applied to the outer wall 882 of the upright 874 of the retainer 870. When the blade & retainer assembly 950 is inserted and seated into the annular groove 768 of the blade housing portion 762, the outer wall 882 is bonded to the outer wall 767 of the housing portion 762. Some of the adhesive flows down and bonds the upper surface 886 to the portion 888 of the bottom wall 765 of the annular ring 763. In one exemplary embodiment, both the retainer 870 and the blade support assembly 760 are fabricated of PPS, thus, a suitable adhesive would be an cyanoacrylate adhesive such as Apollo H7 single component cyanoacrylate adhesive sold by Cyberbond LLC, 401 North Raddant Road, Batavia, Ill. 60510. Another exemplary method of affixing the retainer 870 to the blade housing portion 762 would be fusing them together via ultrasonic welding. Accordingly, by virtue of the retainer 870 being permanently bonded to the blade housing portion 762 of the disposable blade support assembly 760, the blade 900 is permanently supported for rotation within the annular groove 768, while the retainer 870 is permanently affixed to the blade housing portion 762 and is stationary with respect to the rotating blade 900. Stated another way, by virtue of the retainer 870 being permanently bonded to the blade housing portion 762, the blade & retainer assembly 950 becomes permanently affixed to the blade housing portion 762 of the disposable blade assembly 760.

The inner wall 878 of the upright 874 and the inner, upper surface 880 of the base 872 form an L-shaped bearing surface 889 providing for rotation of the blade 900 with respect to the retainer 870 and the blade housing portion 762. The L-shaped bearing surface 889 of the retainer 870 provides both vertical and horizontal bearing surfaces for the body support section 904 of the blade 900. The top wall 771 defining the annular groove 768 also serves as a horizontal bearing surface for the body support section 904 of the blade 900, while the inner wall 769 defining the annular groove 768 also serves as a vertical bearing surface for the body support section 904 of the blade.

It should be appreciated that not all of the mating bearing surfaces of the blade 900, the retainer 870, the radial inner wall 769 of the annular groove 768, and the top wall 771 of the annular groove 768, as described above, are in contact at any given time because there are necessarily running clearances between the blade and the retainer which allow the blade to rotate relatively freely within a region defined by the retainer 870 and the blade housing annular groove 768. As explained above, these running clearances cause the blade 900 to act somewhat akin to a teeter-totter within the blade housing retainer 870 and the annular groove 768, that is, as one region of the blade is pivoted or moved upwardly within the retainer and annular groove during a cutting or trimming operation in a bone debriding process, the diametrically opposite portion of the blade (180° away) is pivoted or moved downwardly within the retainer and annular groove. Accordingly, the mating bearing surfaces in contact at a specific location of the blade-retainer-annular groove interface will change and, at any given time, will be determined by the forces applied during use of the rotary knife.

Third Exemplary Embodiment of Blade Retainer Structure 1150

Figure 24:
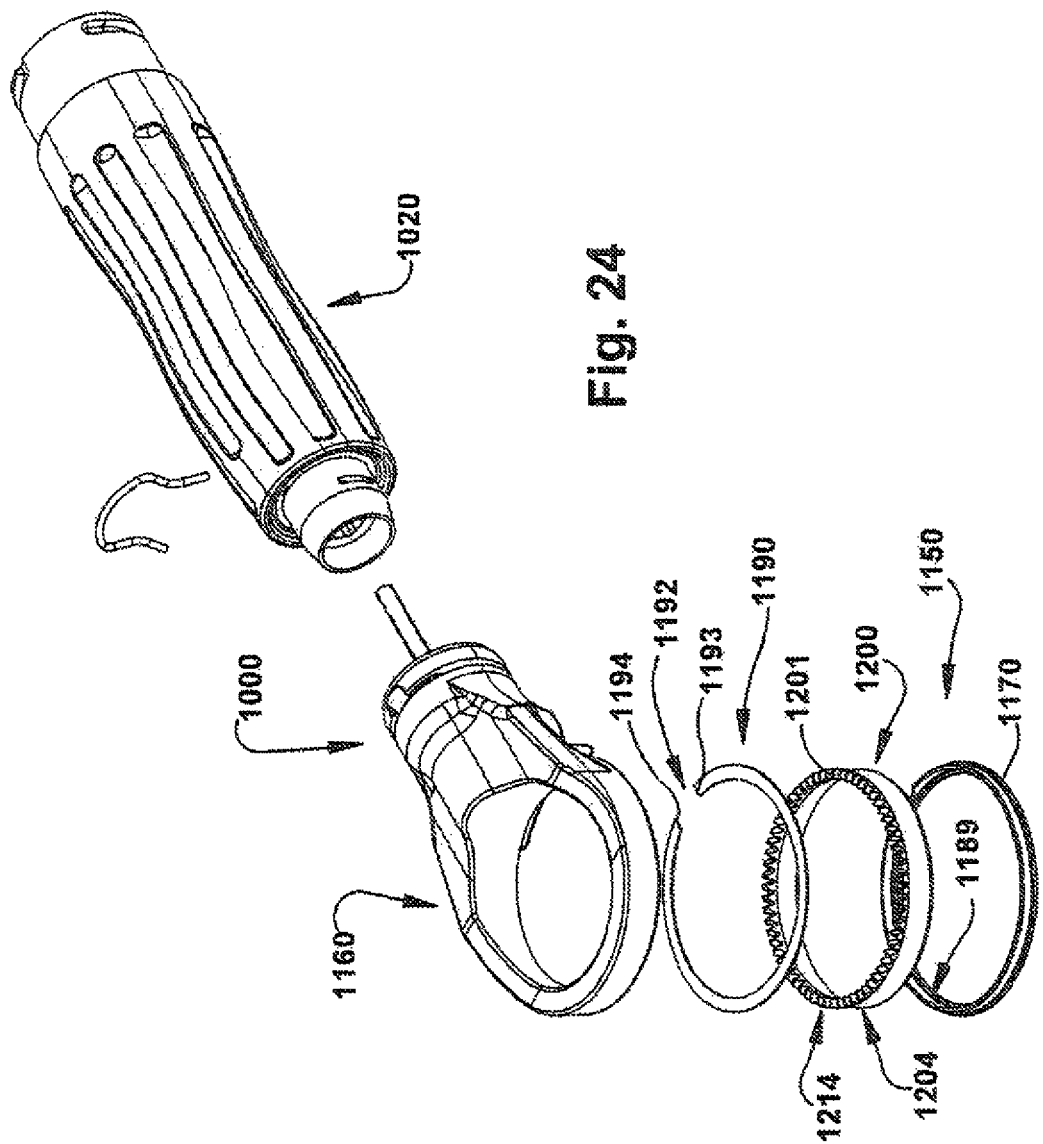
FIG. 24 is a schematic perspective view of a portion of the power operated rotary knife of FIG. 1 showing a disposable blade support assembly and a third blade retainer structure exemplary embodiment to retain an annular rotary knife blade in the disposable blade support assembly, the blade retainer structure including a two piece retainer.
Figure 27:
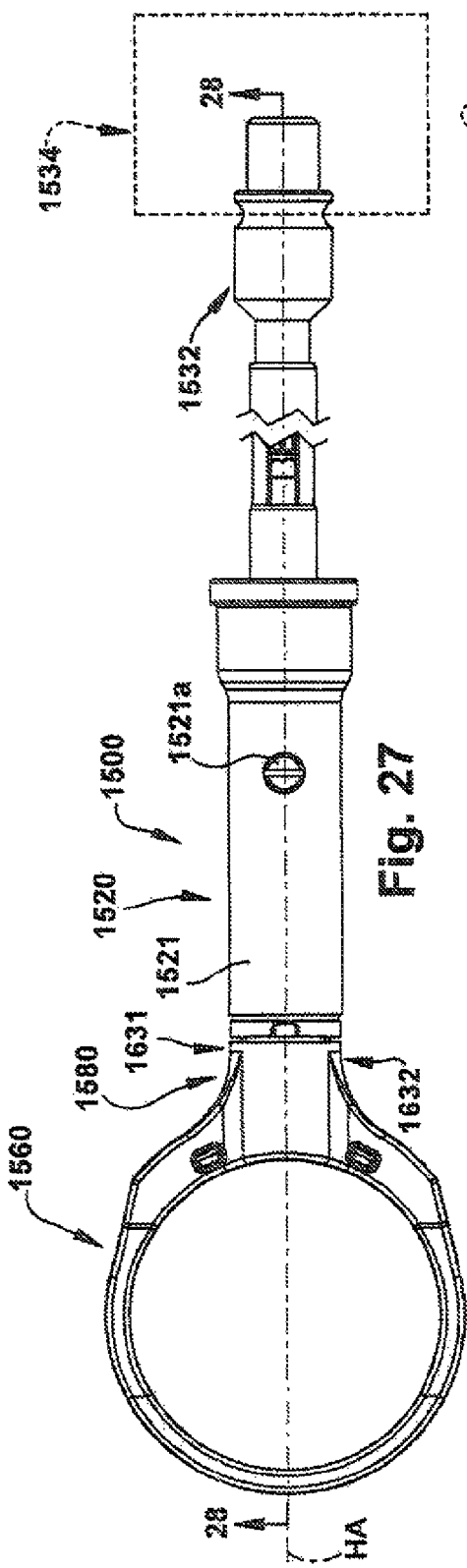
FIG. 27 is a schematic top plan view of an alternate exemplary embodiment of a power operated rotary knife of the present disclosure including a second exemplary embodiment drive assembly and drive gear mechanism that includes a flexible drive shaft that extends through a longitudinal opening though the handle assembly to drive an alternate exemplary embodiment of an annular rotary knife blade.

FIGS. 24-26 schematically depict a rotary knife 1000 of the present disclosure including a third exemplary embodiment of a blade retainer structure 1150 that retains and permits rotation of an annular rotary knife blade 1200 within an annular groove 1068 of the blade housing portion 1062 of the disposable blade support assembly 1060. For simplicity, only the differences from the prior embodiment will be described herein, it being understood that the overall configuration and operation of the rotary knife 1000 of the present embodiment is substantially the same as the rotary knife 10 of the first embodiment.

In this embodiment, the rotary knife 1000 includes the reusable handle assembly 1020 and the disposable blade support assembly 1060. The blade retainer structure 1150, in the third exemplary embodiment is identical to the blade retainer of the second embodiment, i.e., blade retainer structure 850, including the blade retainer 870, with the addition of an extra component, namely, a washer 1190 which is inserted between an upper axial surface 1201 of the blade 1200 and the top wall 1071 defining the annular groove 1068. Thus, the blade retainer structure 1150 includes a retainer 1170, like the retainer 850 of the second blade retainer embodiment, and the washer 1190.

The washer 1190 is preferably fabricated of a durable, low friction material such as steel or other metal/metal alloy. The purpose of the washer 1190 is to minimize wear that would otherwise occur between the upper axial surface 1201 which is defined by an upper surface of the plurality of gear teeth 1214 formed in the upper portion of the annular body support section 1204 of the blade 1200 as the blade 1200 is rotating in the annular groove 1068 of the blade housing portion 1062. As can best be seen in FIG. 24, the washer 1190 is not a complete annulus. Rather, the washer 1190 includes a cut out region 1192 that provides clearance for the pinion gear clearance opening 1191 of the main body region 1185 of the head portion 1180.

Unlike the retainer 1170, the washer 1190 is not bonded to the blade housing portion 1062. Instead, the washer 1190 is inserted in the annular groove 1068 and is held in position axially within the groove by the retainer 1170 when the retainer & blade assembly 1250 is inserted into the groove and the retainer 1170 is bonded to the blade housing portion 1062, as described above. Specifically, as can be seen in FIG. 26, when the retainer 1170 is bonded to the blade housing portion 1062, an upper surface 1184 of the upright 1174 is in contact with and bears against the washer 1190 preventing it from moving axially within the blade housing portion annular groove 1068. Additionally, the washer 1190 is prevented from moving radially within the annular groove 1068 by downwardly extending bumps (not shown) formed on the top wall 1071 of the annular groove 1068. The bumps are disposed within the washer cut out region 1192 adjacent the ends 1193, 1194 of the washer. The bumps preclude the washer 1190 from rotating in the direction of the blade rotation within the groove 1068.

The inner wall 1178 of the upright 1174 and the inner, upper surface 1180 of the base 1172 form an L-shaped bearing surface 1189 providing for rotation of the blade 1200 with respect to the retainer 1170 and the blade housing portion 1062. The L-shaped bearing surface 1189 of the retainer 1170 provides both vertical and horizontal bearing surfaces for the body support section 1204 of the blade 1200. The lower surface 1196 of the washer 1190 also serves as a horizontal bearing surface for the body support section 1204 of the blade 1200, while the inner wall 1069 defining the annular groove 1068 also serves as a vertical bearing surface for the body support section 1204 of the blade 1200.

It should be appreciated that not all of the mating bearing surfaces of the blade 1200, the retainer 1170, the washer 1190, and the radial inner wall 1069 of the annular groove 1068, as described above, are in contact at any given time because there are necessarily running clearances between the blade and the retainer which allow the blade to rotate relatively freely within a region defined by the retainer 1170, the washer 1190, and the blade housing annular groove 1068. As explained above, these running clearances cause the blade 1200 to act somewhat akin to a teeter-totter within the blade housing retainer 1170, the washer 1190, and the annular groove 1068, that is, as one region of the blade is pivoted or moved upwardly within the retainer and annular groove during a cutting or trimming operation in a bone debriding process, the diametrically opposite portion of the blade (180° away) is pivoted or moved downwardly within the retainer and annular groove. Accordingly, the mating bearing surfaces in contact at a specific location of the blade—retainer—washer—annular groove interface will change and, at any given time, will be determined by the forces applied during use of the rotary knife.

Second Exemplary Embodiment of Blade Support Assembly 1560 and Drive Assembly 1525

In the previously described embodiments of the power operated rotary knife of the present disclosure, the reusable handle assembly 20 included a drive assembly 25 in which motive power for rotating the annular blade 200 was provided by an air motor 26 disposed in the longitudinal throughbore 24 of the handle inner sleeve 22. In previously described embodiments of the power operated knife of the present disclosure, the disposable blade support assembly 60 included a drive gear mechanism 92 in which the pinion gear 97 was supported for rotation within a cylindrical opening or cavity 84 and the pinion gear was held in place within the head portion cavity 84 by a retainer ring 86 with a plurality of flexible tabs 87 which flexed and contacted the cylindrical wall 133a defining the socket opening 133.

In an alternate exemplary embodiment shown in FIGS. 27-30, a power operated rotary knife 1500 of the present disclosure includes a reusable handle assembly 1520 that utilizes a drive assembly 1525 that includes a flexible drive shaft assembly 1526 that extends through a longitudinal throughbore 1524 of an elongated handle 1521, in place of the air motor 26 of the previous embodiments. The handle 1521, in the illustrated exemplary embodiment, is a one-piece, plastic member capable of being sterilized at high temperatures, as opposed to the two-piece structure of the previous embodiments. Alternately, the handle 1521 may be a one-piece metal member, also capable of withstanding the high temperatures required by sterilization methods. The flexible drive shaft assembly 1525 includes a stationary outer sheath 1528 and an inner rotatable drive shaft 1527. In one exemplary embodiment, the end portions of the drive shaft 1527 are substantially square in cross section. The opposite end portions of the drive shaft assembly 1525 include couplings 1530, 1532. The proximal end coupling 1532 engages an external motor 1534 (shown schematically in dashed line in FIGS. 27 & 28), such as an AC electric motor to rotate the drive shaft 1527.

Figure 29:
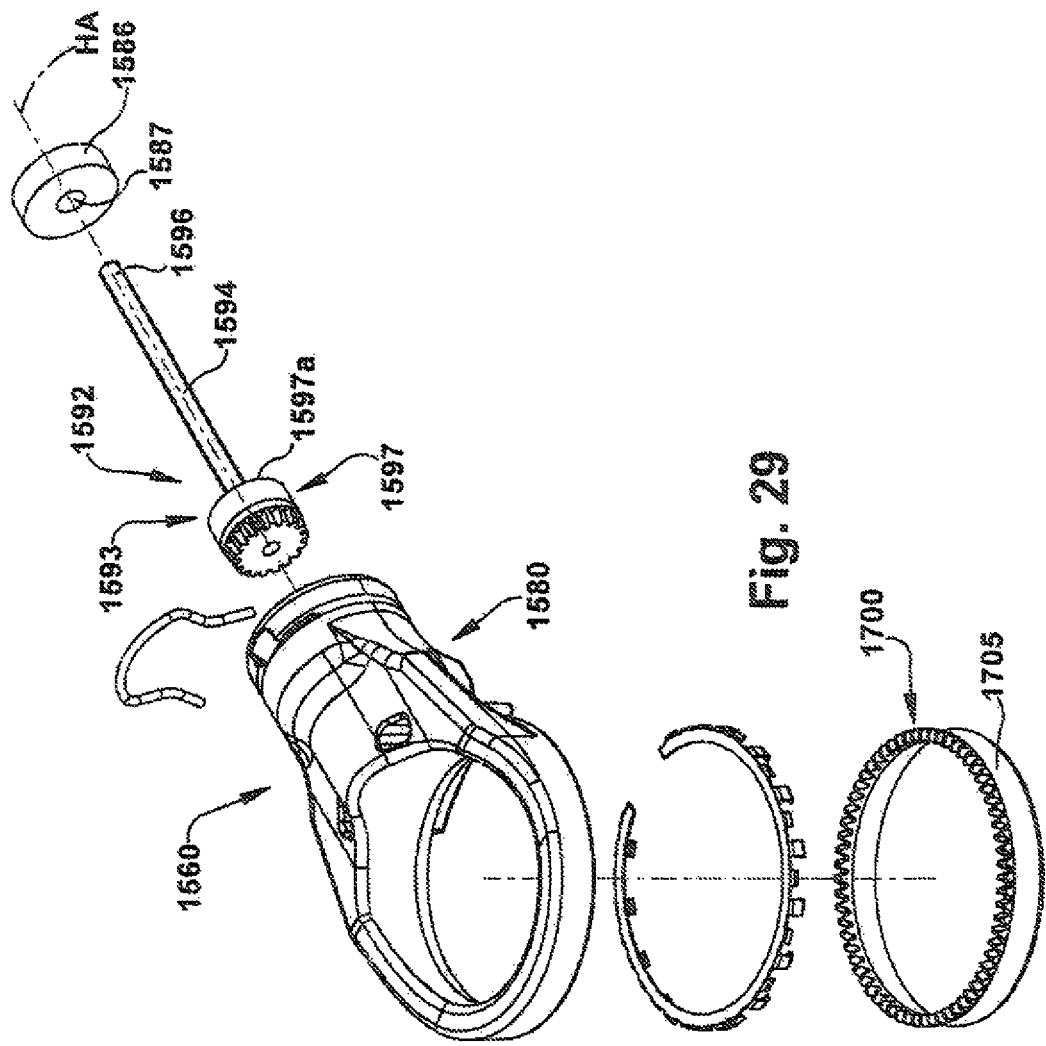
FIG. 29 is an exploded perspective view of the disposable blade support assembly of the power operated rotary knife of FIG. 27.

The disposable blade support assembly 1560 is shown in FIG. 29 and includes a drive gear mechanism 1592 that is modified from the drive gear mechanism 92 of the first embodiment. The drive gear mechanism 1592 includes a pinion gear assembly 1593 including a pinion gear 1597 and a driven shaft 1594 extending rearwardly from a central longitudinal axis of the pinion gear 1597 which is substantially congruent with the handle axis HA. However, unlike the prior embodiments, the pinion gear 1597 is not supported for rotation by a cylindrical cavity in the head portion with the wall of the cavity functioning as a bearing, rather the driven shaft 1594 and the pinion gear 1597 are supported for rotation by a ring-shaped bushing 1586 that abuts a rearward or proximal back wall 1597a of the pinion gear. As can best be seen in FIG. 29, the bushing 1586 includes a central opening 1587 that allows the bushing to slide onto the driven shaft 1594. Compared to the previous embodiments, the pinion gear 1597 is reduced or shortened in longitudinal extent to allow room for the bushing 1586.

The size of the cylindrical pinion gear cavity 1584 formed in the head portion 1580 is large enough to provide clearance such that the pinion gear 1597 does not ride on the wall 1584a defining the cavity, as in the previous embodiments. Instead, the cavity 1584 has clearance built in and the pinion gear is supported for rotation by the driven shaft 1594 and the bushing 1586. The bushing 1586 is pressed into and supported within a slightly larger diameter cylindrical opening 1633 defined by the socket 1632 of the cylindrical interface region 1631. In one exemplary embodiment, the bushing 1586 is comprised of temperature-resistant plastic material such as polyetheretherketone (PEEK) or some other suitable material. The wall 1633a defining the cylindrical opening 1633 includes a plurality of inwardly extending ribs that bear against outer surface of the bushing 1586 to hold the bushing and the pinion gear 1597 in place. The ribs of the wall 1633a mitigate the necessity of holding a tight tolerance on the cylindrical opening 1633.

Figure 28:
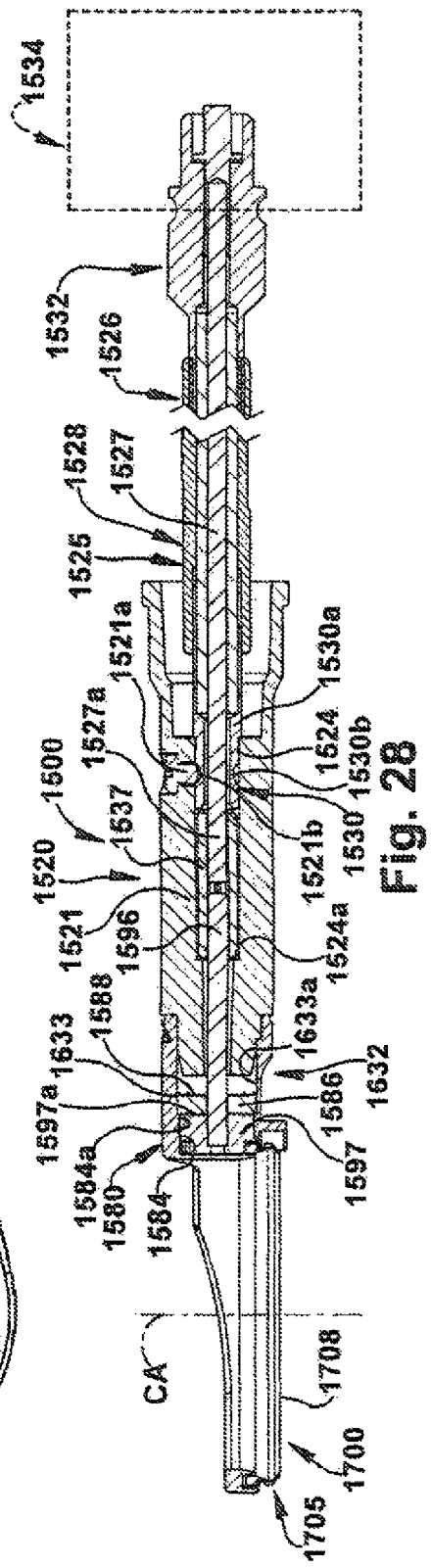
FIG. 28 is a schematic longitudinal sectional view of the power operated rotary knife of FIG. 27, as seen from as seen from a plane indicated by the line 28-28 in FIG. 27.

As is best seen in FIG. 28, the transmission of rotational power from a distal end 1527a of the flex shaft assembly drive shaft 1527 to the driven shaft 1594 of the pinion gear assembly 1593 is provided by a tubular coupling 1537 supported for rotation with the handle longitudinal throughbore 1524. The tubular coupling 1537 includes a cylindrical outer surface for rotation within the handle throughbore 1524 and a square central opening to receive a proximal end 1596 of the driven shaft 1594 and a distal end 1527a of the drive shaft 1527. A distally extending casing 1530a of the distal coupling 1530 of the drive shaft assembly 1525 holds the tubular coupling 1537 in place against an inwardly stepped portion 1524a of the throughbore 1524. The casing 1530a and therefore the distal coupling 1530 of the drive shaft assembly 1526 are held in place with respect to the handle 1521 by a screw 1521a. When the screw 1521a is threaded through a threaded radial opening in the handle 1521, a rounded distal end 1521b extends into and bears against a groove 1530b formed in an outer wall of the casing 1530a to secure the casing and the distal coupling 1530 in place. When the screw 1521a is removed, the coupling 1537 may be removed from the handle 1521 and the tubular coupling 1537 will fall out of the throughbore 1524 to facilitate sterilization of the handle assembly 1520. In this embodiment of the handle assembly 1520, the ends of the handle 1521 do not need to be plugged or capped prior to sterilization. Rather, the entire handle 1521 may be subjected to sterilization without protection.

It should be understood that depending on the debriding task to be performed, different types and sizes of annular knife blades may be utilized. As can best be seen in FIG. 28, the annular knife blade 1700 is of different configuration than the knife blade 200 of the previous embodiments in that the blade section 1705 is "hooked" and extends radially inwardly toward the central axis CA of the blade when moving in the direction of the cutting edge 1708.

While a given rotary knife of the present disclosure, as explained previously, has a specific annular blade permanently installed in the disposable blade support assembly, the lower cost of the disposable blade support of the present disclosure afforded by the unitary, plastic main body portion will facilitate purchasing of several different models having different blade section configurations and different blade diameters.

For example, looking at the rotary knife blade 900 shown in FIG. 22, the blade includes a blade section 905 that is angled slightly outward away from the central axis CA of the blade. Such a blade is referred to as a straight blade is particularly useful when making deep or plunge cuts into tissue. By contrast, the blade shown in FIGS. 27-29 includes a radially inwardly curved blade section 1705, generally referred to as a hooked blade. Such a hooked blade type is particularly suited to making trimming layers of tissue while cutting in a sweeping motion.

If it is desired to be able to efficiently trim relatively thin, but wider layers of tissue, selecting a blade with a larger blade diameter will generally be advantageous. On the other hand, if it is desired to be able to make deeper and narrower cuts, selecting a blade with a smaller blade diameter will generally be advantageous. Annular blade diameters typically range from approximately 1.5 to more than 5 inches. The present disclosure contemplates annular blades with various blade section configurations and blade diameters, the configuration and diameter to be matched to the type of cutting or trimming that the rotary knife is expected to be predominantly used in connection with.

Method of Debriding Tissue Using Power Operated Rotary Knife 10

A method of debriding tissue using any of the power operated rotary knifes of the present disclosure, for example, the power operated rotary knife 10, is schematically shown generally at 2000 in FIGS. 30-33. A bone of a donor body (human or otherwise) is shown generally at 2001. The bone 2001 may be connected to other bones 2002 in the donor via connective tissue. A ball and socket arrangement is shown schematically between bones 2001, 2002. A layer of tissue 2003 is to be removed from an upper, outer surface 2004 of the bone 2001. The tissue may comprise, skin, muscle, fat, connective tissue, etc. The tissue 2003 may be tissue that is desired, in and of itself, for recovery and future use or the tissue 2003 may be tissue that is not desired for recovery but is only being removed for purposes of debriding/cleaning of tissue from the bone 2001 such that the bone may be recovered for future use.

Figure 31:
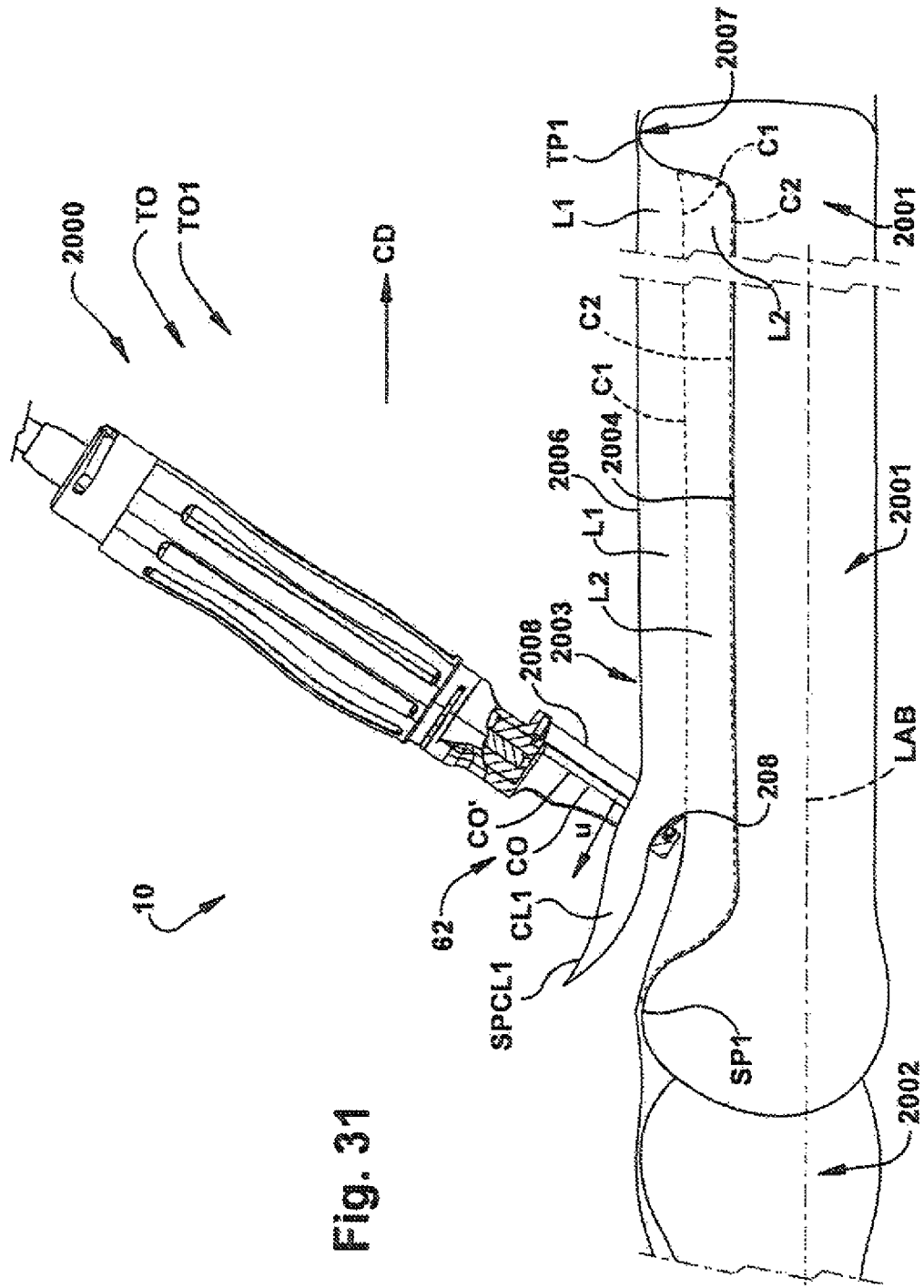
Figure 32:
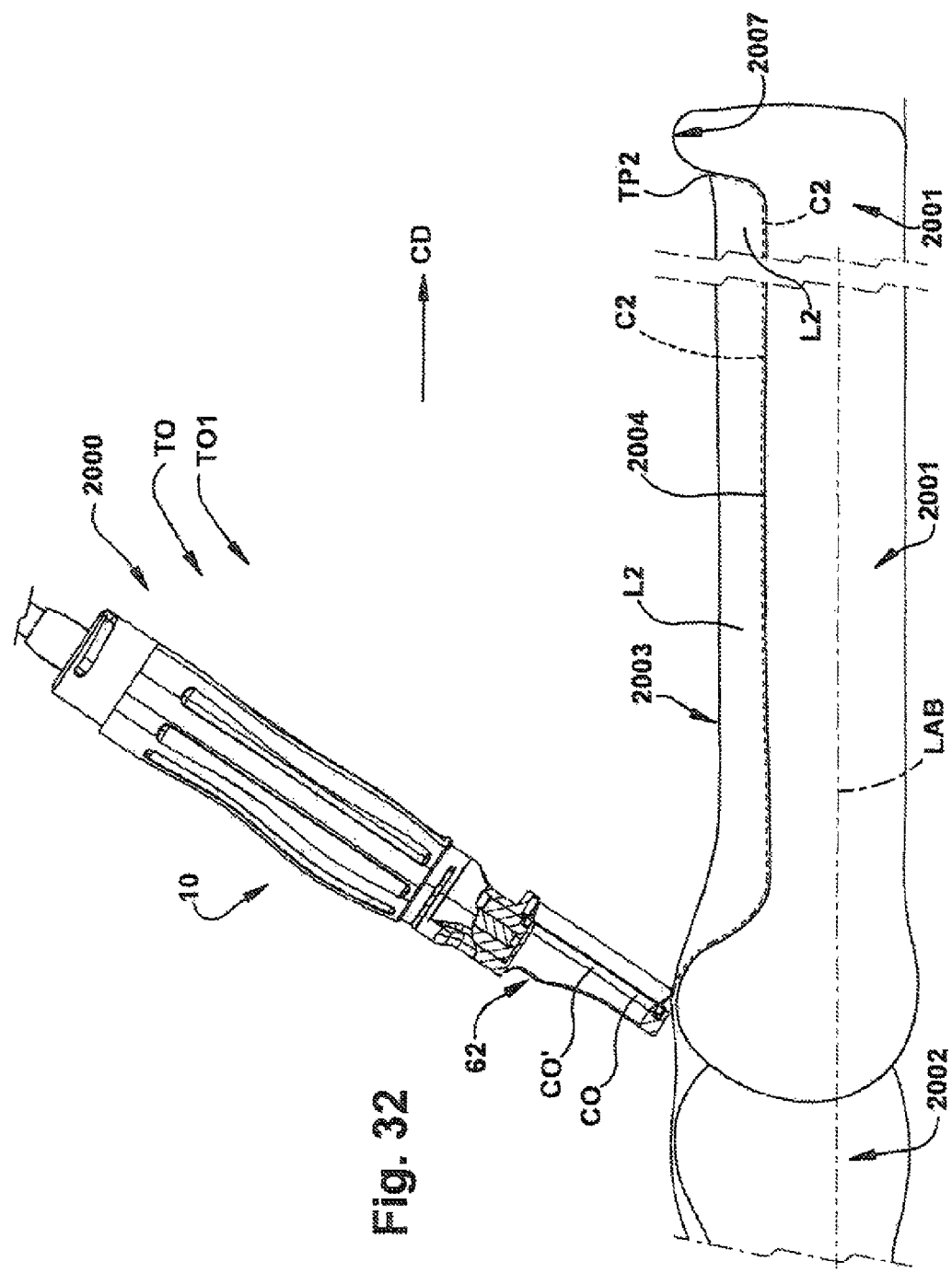
Figure 33:
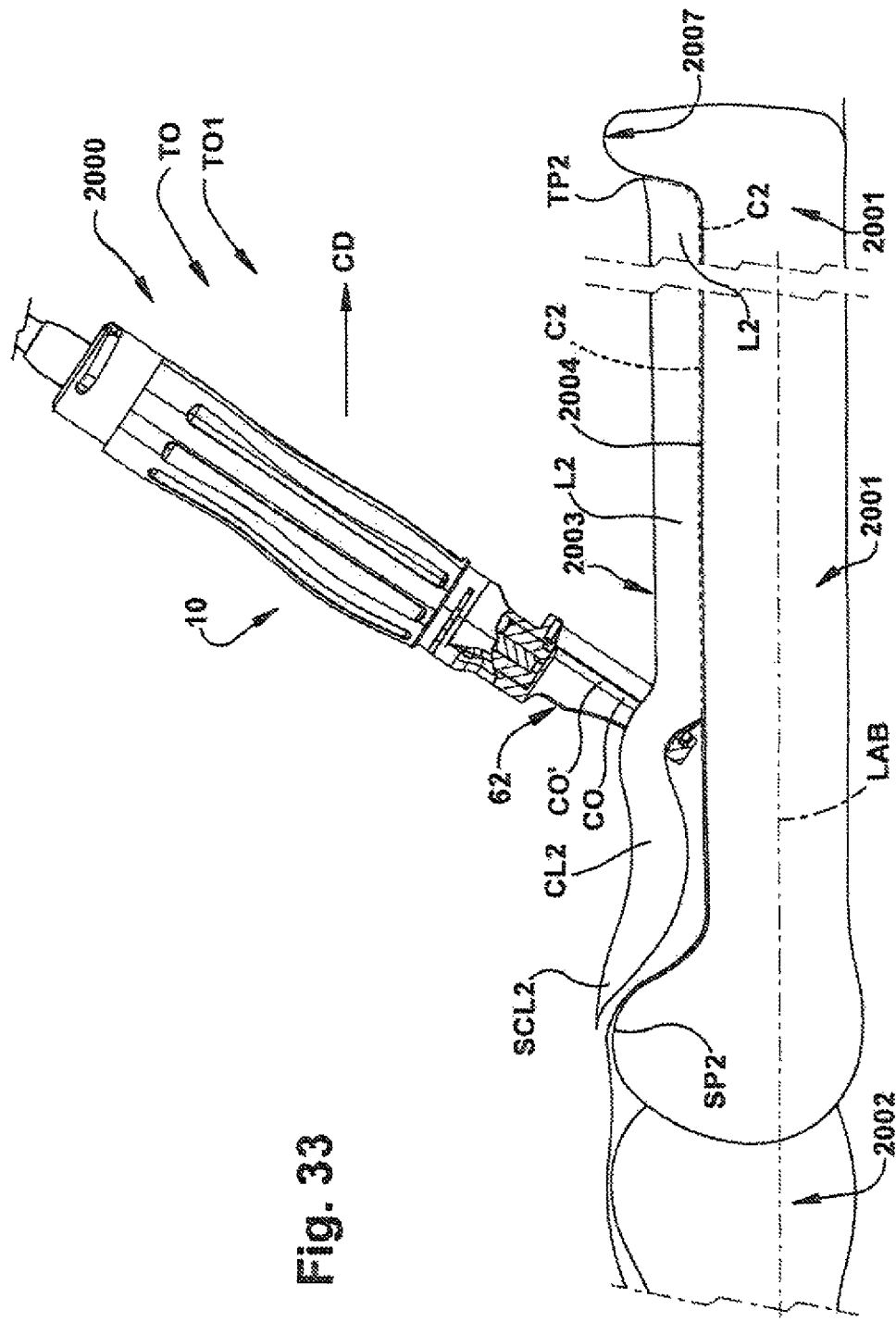

The thickness of the tissue layer 2003 to be removed may necessitate that multiple layers be cut from the bone 2001 in order to remove all or enough of the tissue 2003 from the bone outer surface 2004 such that subsequent processing of the debrided bone can commence. In the illustrative example shown in FIGS. 30-33, because of the thickness of the tissue layer 2003, two layers L1, L2 of tissue 2003 must be cut or trimmed from the bone 2001 to remove substantially all of the tissue 2003 from the bone outer surface 2004. A trim or cut line C1 schematically represents a path of travel of the blade cutting edge 208 to remove tissue layer L1 from the bone 2001, while trim or cut line C2, which is adjacent to the bone outer surface 2004, schematically represents a path of travel of the blade cutting edge 208 to remove tissue layer L2 from the bone 2001. That is, the overall tissue debriding operation TO will include a first trimming operation TO1 to remove tissue layer L1 from the bone 2001 (FIGS. 30 & 31) and a second trimming operation TO2 to remove tissue layer L2 from the bone 2001 (FIGS. 32 & 33). The rotary knife 10 is moved from left to right in the Figures, that is, in a cutting direction CD in the Figures to trim tissue layers L1 and L2.

Figure 30:
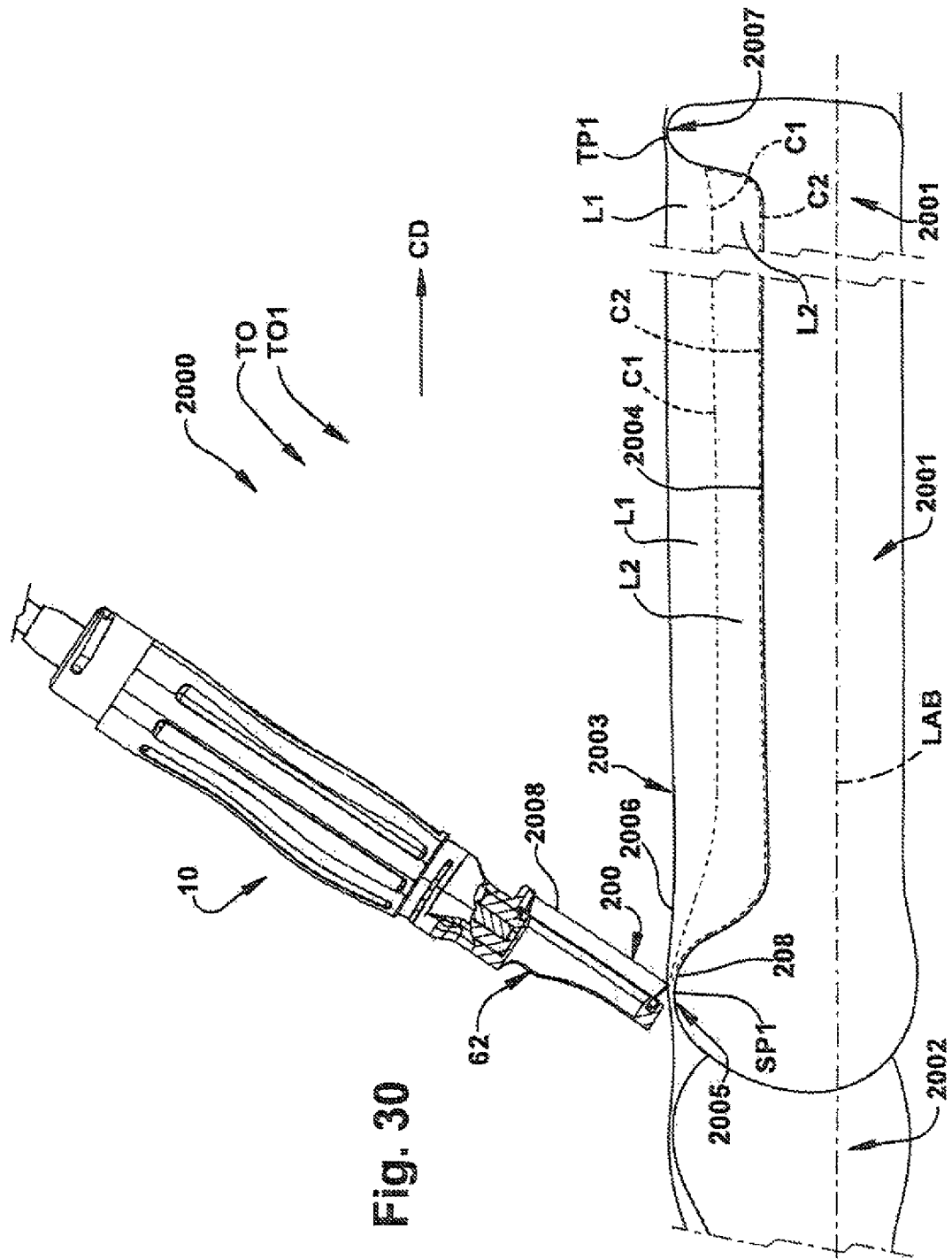
FIGS. 30-33 are schematic depictions of a power operated knife of the present disclosure used in a method of debriding or removing tissue from a bone.

As can be seen in FIG. 30, the trimming of the first tissue layer L1 is initiated at a starting point SP1. The blade cutting edge 208 is brought to bear against the outer or skin layer 2006 of the tissue layer 2003 and the knife 10 is manipulated to cut into the skin layer 2006 and continue the trimming along the cutting line C1 (FIG. 31). This results in a cut layer CL1 corresponding to the layer 1. In this case, the starting point SP1 may be at an upper, end portion 2005 of the bone 2001, where it is closest in proximity to an outer or skin layer 2006 of the tissue 2003. This is convenient because where the tissue layer 2003 is relatively thin over the end portion 2005 of a bone 2001, the end portion of the bone may be readily identified by the operator. However, it is not necessary that the cutting starting point SP1 be at or near an end portion 2005 of the bone 2001. Depending on the operator position with respect to the knife 10 and the bone 2001, the length of the operator's arms, the amount and configuration of the tissue 2003 to be removed, etc., the operator may select another starting point.

As can be seen in FIG. 31, for the first trimming operation TO1, the knife 10 is moved in the direction CD and the blade cutting end 208 follows a path of travel along cutting path C1 to remove tissue layer L1. The cut portion CL1 of the first layer L1 moves through the central openings CO, CO' of the blade 200 and blade housing portion 62, respectively as the blade cutting edge 208 moves along the cut path C1. The first trim cut portion CL1 in the vicinity of the starting point SP1 is generally wedge shaped at the distal end SPCP1 of the cut portion CL1. This is because as the cut is initiated at the starting point SP1, the blade edge 208 will move simultaneously downwardly toward the bone 2001 and forwardly in the cutting direction CD and will contact and move along the upper surface of the 2004 of the bone 2001 as it moves along the cutting path C1. Thus the end SPCP1 of the cut portion C1 will be generally wedge shaped.

The cut path C1 terminates at a termination point TP1 (FIG. 31), typically, the termination point TP1 may be at or near the opposite end portion 2007 of the bone 2001 being debrided. If the bone 2001 is unusually short or unusually long the termination point may not coincide with the end portion of the bone as the operatory may make a longer or shorter cut given his or her arm length, position of the knife 10 with respect to the operator, the resistance of the tissue L1 to being cut, etc. After the termination point TP1 is reached the first trim TO1 is complete and the trimmed layer L1 of tissue is removed from the debriding region (i.e., the bone 2001) such that a second trimming operation may be commenced without interference from the first trimmed layer L1 which is detached from the bone 2001 and the remaining tissue.

As can be seen in FIGS. 32 and 33, the tissue debriding process TO includes repeating the trimming operation for a second trim TO2 to trim tissue layer L2 from the bone 2001. Here, in the second trimming operation TO2, the cut path C2 is along the surface 2004 of the bone 2001 that is, the blade cutting edge 208 generally follows the outer surface 2004 of the bone 2001. After the second trim TO2 is complete, the surface 2004 of the bone 2001 is substantially free from tissue and the debrided bone is ready for further processing. In some instances, further processing of the debrided bone may include, for example, removal of residual tissue after trimming is completed by dipping the bone 2001 in a chemical bath or rinsing the bone with chemicals to remove some or all of the residual tissue. Generally, the tissue debriding steps of: 1) trimming a layer of tissue from the bone; and 2) removing the trimmed layer of tissue is repeated as many times as necessary such that the desired tissue is obtained, e.g., the bone 2001 is sufficiently debrided or has sufficient tissue removed for further processing or storage of the debrided bone.

It should be recognized that the schematic depictions of the first and second trimming operations TO1, TO2 are shown in two dimensions. In fact, the bone 2001 is three dimensional. Thus, the cleaned or debrided area of the bone outer surface 2004 resulting from the first and second trimming operations TO1, TO2 when viewed in three dimensions would appear somewhat like a long rectangular cleaned area on the outer surface 2004 of the bone 2001 extending in a direction along a longitudinal axis LAB of the bone 2001. To clean or debride the entirety of the outer surface 2004 of the bone 2001, the trimming operation TO would have to be repeated numerous times around the three dimensional outer peripheral surface 2004 of the bone 2001.

As seen in FIG. 32, the starting point SP2 for the second trim layer L2 will typically be close to but slightly offset from first trim starting point SP1. This is because when the first trim TO1 is initiated, some of the tissue along the outer surface 2004 of the bone 2001 will be removed thereby leaving the outer surface of the bone 2001 bare or clean in the vicinity of SP1 and there is no sense in attempting to trim a portion of the bone 2001 that is already clean or debrided. Thus, as can be seen in FIGS. 32 and 32, second starting point SP2 is slightly beyond (in the direction CD) the first starting point. From the second starting point SP2, the knife 10 is moved in the direction CD to remove the second trim layer TO2.

Similarly, the termination point TP2 of the second trim will be near but slightly offset from the first termination point TP1 because the outer surface 2004 of the bone 2001 is likely clean in the vicinity of TP1. Thus, the second termination point TP2 will fall somewhat short of the first termination point TP1 with respect to the second end portion 2007 of the bone 2001.

As used herein, terms of orientation such as upper, lower, inward, outward, forward, rearward, proximal, distal, etc., are provided for convenience purposes and relate generally to the orientation shown in the Figures. Such orientation terms are not intended to limit the scope of the present disclosure or the claims appended hereto.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A method of debriding tissue utilizing a power operated rotary knife, the steps of the method comprising:
a) providing a power operated rotary knife having a handle assembly and a blade support assembly coupled to the handle assembly, the blade support assembly including: a blade housing portion including an annular ring and defining an annular groove in a bottom surface of the annular ring; an annular rotary knife blade supported for rotation within the annular groove of the blade housing portion, the blade having first and second axially spaced apart ends and an annular body extending therebetween, the annular body including a plurality of gear teeth at the first end and an annular blade section adjacent the second end; and a retainer securing and rotatably supporting the annular body of the knife blade within the annular groove, the retainer affixed within the annular groove and including an upper wall, a first plurality of tabs and a second plurality of tabs, wherein the first plurality of tabs contact a wall of the annular groove to permanently affix the retainer within the annular groove and further wherein the second plurality of tabs define a bearing race to rotatably support the annular body of the annular rotary knife blade;
b) using the power operated rotary knife to trim a layer of tissue; and
c) removing the trimmed layer of tissue.

2. The method of claim 1, wherein steps b) and c) are repeated until all desired tissue has been debrided.

3. The method of claim 1, wherein an elongated handle of the handle assembly is grasped and manipulated to trim the layer of tissue.

4. The method of claim 1, wherein step b) includes the substeps of:
i) initiating a cut at a selected starting point on the layer of tissue to be trimmed by moving the power operated rotary knife such that the cutting edge of the annular blade section of the annular rotary knife blade is brought to bear against an outer layer of the layer of tissue;
ii) moving the power operated rotary knife in a cutting direction whereby the cutting edge of the annular blade section of the annular rotary knife blade moves along a cutting path through the layer of tissue; and
iii) terminating the cut at a selected termination point.

5. The method of claim 1, wherein the first plurality of tabs have an interference fit with a radially outer wall of the annular groove.

6. The method of claim 1, wherein the second plurality of tabs each includes first and second portions forming a generally L-shaped radially inwardly facing bearing race.

7. The method of claim 1, wherein the first plurality of tabs extend from the upper wall of the retainer.

8. The method of claim 7, wherein the first plurality of tabs have an interference fit with a radially outer wall of the annular groove.

9. The method of claim 1, wherein the second plurality of tabs extend from the upper wall of the retainer.

10. The method of claim 9, wherein the second plurality of tabs each includes first and second portions forming a generally L-shaped radially inwardly facing bearing race.

11. A method of debriding tissue utilizing a power operated rotary knife, the steps of the method comprising:
a) providing a power operated rotary knife having a handle assembly and a blade support assembly coupled to the handle assembly, the blade support assembly including: a head portion; a blade housing portion extending from a distal end of the head portion, the blade housing portion including an annular ring and defining an annular groove in a bottom surface of the annular ring; an annular rotary knife blade permanently supported for rotation within the annular groove of the blade housing portion, the annular rotary knife blade having first and second axially spaced apart ends and an annular body extending therebetween, the annular body including a plurality of gear teeth at the first end and an annular blade section adjacent the second end; a drive gear mechanism rotatably supported within the head portion and including a plurality of gear teeth that mesh with the plurality of gear teeth of the annular body support section to rotate the annular rotary knife blade; and a retainer structure including a retainer rotatably supporting the annular body of the annular rotary knife blade within the annular groove, the retainer permanently affixed within the annular groove, wherein the retainer includes an upper wall, a first plurality of tabs and a second plurality of tabs, wherein the first plurality of tabs extend from the upper wall and contact a wall of the annular groove to affix the retainer within the annular groove and wherein the second plurality of tabs extend from the upper wall and define a bearing race to rotatably support the annular body of the annular rotary knife blade;

b) using the power operated rotary knife to trim a layer of tissue; and c) removing the trimmed layer of tissue.

12. The method of claim 11, wherein steps b) and c) are repeated until all desired tissue has been debrided.

13. The method of claim 11, wherein an elongated handle of the handle assembly is grasped and manipulated to trim the layer of tissue.

14. The method of claim 11, wherein step b) includes the substeps of:

i) initiating a cut at a selected starting point on the layer of tissue to be trimmed by moving the power operated rotary knife such that the cutting edge of the annular blade section of the annular rotary knife blade is brought to bear against an outer layer of the layer of tissue;

ii) moving the power operated rotary knife in a cutting direction whereby the cutting edge of the annular blade section of the annular rotary knife blade moves along a cutting path through the layer of tissue; and iii) terminating the cut at a selected termination point.

15. The method of claim 11, further including an interface structure disposed at a proximal end of the blade support assembly, the interface structure engaging an interface element of the handle assembly to releasably attach the blade support assembly to the handle assembly.

16. The method of claim 11, wherein the first plurality of tabs of the retainer extend radially outwardly and downwardly from the upper wall, the second plurality of tabs extend radially outwardly and downwardly from the upper wall and have an interference fit with the wall of the annular groove, and the second plurality of tabs each has first and second portions forming a generally L-shaped radially inwardly facing bearing, the generally L-shaped radially inwardly facing bearing defines the bearing race to rotatably support the annular body support section of the blade.

17. The method of claim 16, wherein for each of the second plurality of tabs, the first portion extends axially downwardly along a radially outer surface of the annular body support section of the annular rotary knife blade and the second portion extends radially inwardly along a lower surface of the annular body support section of the annular rotary knife blade.

18. The method of claim 11, wherein the drive gear mechanism includes a cylindrically-shaped pinion gear supported for rotation in an interior region in the head portion adjacent to and extending from the interface region opening, the plurality of gear teeth of the drive gear mechanism comprising axially extending teeth defined at a first end of the pinion gear, the drive gear mechanism further including a drive shaft extending from the pinion gear into the longitudinal throughbore of the handle assembly.

19. The method of claim 18, wherein the drive mechanism further includes a retaining ring adjacent a second end of the pinion gear, the retaining ring including a plurality of radially outward extending tabs that bear against an interior wall of the head portion defining the head portion interior region to secure the pinion gear within the interior region.

20. The method of claim 11, wherein the head portion and the blade housing portion comprise a unitary, one-piece structure.

* * * * *